(12) United States Patent
Schmücker et al.

(10) Patent No.: US 10,835,453 B2
(45) Date of Patent: Nov. 17, 2020

(54) STORAGE-STABLE RESIN-MODIFIED GLASS IONOMER CEMENT

(71) Applicant: VOCO GmbH, Cuxhaven (DE)

(72) Inventors: Simon Schmücker, Cuxhaven (DE); Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 79 days.

(21) Appl. No.: 15/849,839

(22) Filed: Dec. 21, 2017

(65) Prior Publication Data

US 2018/0168938 A1   Jun. 21, 2018

(30) Foreign Application Priority Data

Dec. 21, 2016  (EP) ..................................... 16205915

(51) Int. Cl.
| | |
|---|---|
| *C04B 26/06* | (2006.01) |
| *A61K 6/889* | (2020.01) |
| *C04B 24/42* | (2006.01) |
| *A61K 6/61* | (2020.01) |
| *A61K 6/77* | (2020.01) |
| *A61K 6/887* | (2020.01) |
| *C04B 111/00* | (2006.01) |
| *C04B 103/00* | (2006.01) |

(52) U.S. Cl.
CPC ................ *A61K 6/889* (2020.01); *A61K 6/61* (2020.01); *A61K 6/77* (2020.01); *A61K 6/887* (2020.01); *C04B 24/425* (2013.01); *C04B 26/06* (2013.01); *C04B 2103/0062* (2013.01); *C04B 2111/00836* (2013.01)

(58) Field of Classification Search
CPC ................ C04B 24/425; C04B 26/06; C04B 2103/0062; C04B 2111/00836; A61K 6/0835; A61K 6/0091; A61K 6/77; A61K 6/887; A61K 6/61
USPC ....................................................... 523/116
See application file for complete search history.

(56) References Cited

U.S. PATENT DOCUMENTS

| | | | |
|---|---|---|---|
| 2,776,952 A | 1/1957 | Bredereck et al. | |
| 2,779,751 A | 1/1957 | Bredereck et al. | |
| 2,846,418 A | 8/1958 | Bredereck et al. | |
| 2,894,932 A | 7/1959 | Bader et al. | |
| 2,935,489 A | 5/1960 | Bader et al. | |
| 5,154,762 A | 10/1992 | Mitra et al. | |
| 5,501,727 A | 3/1996 | Wang et al. | |
| 5,514,762 A | 5/1996 | Bott et al. | |
| 5,965,632 A | 10/1999 | Orlowski et al. | |
| 7,173,074 B2 | 2/2007 | Mitra et al. | |
| 7,488,762 B2 | 2/2009 | Takano et al. | |
| 2003/0166740 A1 | 9/2003 | Mitra et al. | |
| 2005/0252414 A1 | 11/2005 | Craig et al. | |
| 2006/0030637 A1 | 2/2006 | Mitra et al. | |
| 2006/0247330 A1 | 11/2006 | Takano et al. | |
| 2007/0203257 A1 | 8/2007 | Qian | |
| 2010/0048628 A1 | 2/2010 | Nishi et al. | |
| 2014/0050674 A1* | 2/2014 | Tjaderhane | A61K 6/831 424/49 |
| 2014/0213686 A1 | 7/2014 | Falsafi et al. | |
| 2014/0228474 A1* | 8/2014 | Qian | A61K 6/0835 523/116 |

FOREIGN PATENT DOCUMENTS

| | | |
|---|---|---|
| DE | 2419887 | 11/1974 |
| DE | 2406557 | 8/1975 |
| DE | 2816823 | 10/1978 |
| DE | 19605272 | 8/1996 |
| DE | 19757277 | 6/1999 |
| DE | 19928238 | 12/2000 |
| DE | 10017188 | 10/2001 |
| DE | 10124029 | 11/2002 |
| DE | 60209714 | 10/2006 |
| DE | 102005053775 | 5/2007 |
| DE | 112006001049 | 4/2017 |
| EP | 0023685 | 1/1980 |
| EP | 206074 | 6/1986 |
| EP | 0209700 | 6/1986 |
| EP | 0233544 | 2/1987 |
| EP | 0254185 | 9/1990 |
| EP | 0923924 | 6/1999 |
| EP | 1112995 | 7/2001 |
| EP | 1269968 | 1/2003 |
| EP | 1502569 | 2/2005 |
| EP | 1719657 | 11/2006 |
| EP | 1754465 | 2/2007 |
| EP | 1872767 | 1/2008 |
| EP | 1935393 | 6/2008 |
| EP | 2016931 | 1/2009 |
| EP | 2055324 | 5/2009 |
| EP | 2070506 | 6/2009 |
| EP | 2198824 | 6/2010 |
| EP | 2371346 | 10/2011 |
| EP | 2433612 | 3/2012 |
| EP | 2712888 | 2/2014 |
| FR | 2640503 | 6/1990 |
| GB | 2291428 | 1/1996 |
| WO | 88/05651 | 8/1988 |
| WO | 95/22955 | 8/1995 |
| WO | 95/22956 | 8/1995 |
| WO | 00/25279 | 5/2000 |
| WO | 03/057792 | 7/2003 |
| WO | 2004/043409 | 5/2004 |
| WO | 2016/007453 | 1/2016 |

* cited by examiner

*Primary Examiner* — Hannah J Pak
(74) *Attorney, Agent, or Firm* — Duane Morris LLP; Gregory M. Lefkowitz

(57) ABSTRACT

The present invention relates to a composition for use as component of a multicomponent resin-modified glass ionomer cement, to a multicomponent resin-modified glass ionomer cement and also to a process for the preparation of the corresponding compositions and of cured dental materials. The invention furthermore relates to the corresponding use of one or more compounds (S) selected from the group consisting of sulfinic acids, salts of sulfinic acids and salts of organoboron compounds.

13 Claims, No Drawings

STORAGE-STABLE RESIN-MODIFIED GLASS IONOMER CEMENT

CROSS-REFERENCE TO RELATED APPLICATION

This application claims, under 35 U.S.C. § 119, the priority of European Patent Application No. 16205915.8 filed on Dec. 21, 2016, the disclosure of which is incorporated herein by reference in its entirety.

The present invention relates to a composition for use as component of a multicomponent resin-modified glass ionomer cement, to a multicomponent resin-modified glass ionomer cement and also to a process for the manufacturing of corresponding compositions and preparation of cured dental materials. The invention furthermore relates to the corresponding use of one or more compounds (S) selected from the group consisting of sulfinic acids, salts of sulfinic acids and salts of organoboron compounds.

Multicomponent resin-modified glass ionomer cements are used for the filling of permanent teeth requiring restoration, in particular for the filling of milk teeth, for relining, for core build-up, for the capping of pulp, for sealing, in endodontics, for the preparation of crowns, in geriatric dentistry and especially also for luting of dental and orthodontic devices. The invention relates to such multicomponent resin-modified glass ionomer cements and also to processes for the manufacturing and for the use of these dental masses and also to the polymers prepared from the masses (i.e., cured dental materials).

Multicomponent resin-modified glass ionomer cements (subsequently also described as "resin-modified glass ionomer cements") are known from the state of the art; they are, e.g., made by addition of resin components to conventional glass ionomer cements.

The original objective in the development of resin-modified glass ionomer cements was to improve the physical properties and to simplify the handling of conventional glass ionomer cements. Conventional glass ionomer cements exhibit, in contrast to composite materials, lower abrasion resistances and tensile strengths, a poorer esthetic appearance and also a high susceptibility to application faults. In particular, glass ionomer cements are, during their application, very sensitive to moisture: if the cement comes into contact with an excess of moisture in an early stage of its curing, such as, for example, with saliva, then the progress of the setting is disrupted, so that the physical properties of the cured cement are worsened. In particular, the set products may then exhibit an increased solubility in the moist environment of the mouth. In order to compensate for these disadvantages, mixed forms have been developed in which the classical ingredients of the known glass ionomer cements have been supplemented by elements of dental resins.

The resin-modified glass ionomer cements thus produced have a markedly reduced solubility and better mechanical properties than conventional glass ionomer cements. An essential aspect in this improvement is the rapid curing and the more hydrophobic nature of the dental material.

In the curing of the resin-modified glass ionomer cements, the monomer mixture first reacts in a fast crosslinking by means of a radical reaction. In this way, the solubility of the remaining cement constituents is considerably reduced, since these are embedded in the polymer matrix, and the material receives a first "degree of hardness". Due to the commencing solidification of the material, the glass ionomer system is less sensitive to moisture and can then, kinetically more slowly, uninhibited, set further by the acid/base reaction of the glass ionomer. A polymer containing carboxylic acid groups reacts hereby with a basic glass composition (analogously to the chemistry in conventional glass ionomer cements). This basic glass composition is also described as "reactive glass powder". The term "reactive glass powder" means that the basic glass is "reactive" towards an acid functional group. The acid/base reaction always requires the presence of water. With resin-modified glass ionomer cements, the resin-modified portion in the total system is present quantitatively in a very much smaller amount than the glass ionomer cement portion. The properties of these hybrid systems are dominated primarily by the glass ionomer used.

Multicomponent resin-modified glass ionomer cements are usually formulated with two components and are, for example, applied as paste/paste systems or in the liquid/paste form. This also applies to multicomponent resin-modified glass ionomer cements according to the invention.

The application of the cements in the paste/paste form, especially in the 1:1 ratio but also in additional graded ratios (e.g., 1:2, 1:3, 1:4 or 1:10), places the highest demands on the formulation of these systems, in particular on the division of the different constituents of the two-component resin-modified glass ionomer cement in the two components. Unlike as in the powder/liquid, powder/paste or paste/liquid systems, paste/paste systems allow a maximum of chemical interactions between the constituents of the respective pastes, which generally lead to a destabilization of the systems over time, so that the shelf life of the pure paste/paste systems is often severely limited in comparison to other application forms. The enormous complexity of these compositions is, inter alia, partly caused by the initiator components, which often exhibit a multitude of constituents.

The curing reaction of the water-soluble polymer containing carboxylic acid groups with the basic glass composition is initiated at the moment when the components are mixed with one another. The reaction (also described as GIC reaction or GIC setting, wherein "GIC" stands for glass ionomer cement) takes place within this context formally as neutralization of the acid groups of the water-soluble polymer containing carboxylic acid groups with the basic glass composition. The glass can, for example, be a strontium aluminum fluorosilicate glass.

In the case of the radical polymerization of resin-modified glass ionomer cements taking place chemically, the GIC setting mechanism and the redox-initiated polymerization begin in parallel chronologically, the radical reaction proceeding kinetically very much faster.

In the case of the radical polymerization of resin-modified glass ionomer cements being induced by light, the polymerization begins chronologically at the moment when a suitable light source activates the monomer mixture. Within this context also, the radical crosslinking proceeds very much faster than the GIC setting.

In the case of the radical polymerization of resin-modified glass ionomer cements taking place both by light and also chemically, the system exhibits three different curing mechanisms with three different kinetic courses.

WO 88/05651 describes a resin-modified radio-opaque glass ionomer cement as relining material of the paste/paste type which is cured either chemically or by means of light.

U.S. Pat. No. 5,154,762 discloses a resin-modified glass ionomer cement in a triple cure modus which cures in a glass ionomer cement reaction, in a chemically induced crosslinking and in a photopolymerization.

DE 39 41 629 C2 reports about a resin-modified glass ionomer cement of the powder/liquid, paste/liquid or paste/paste type which cures chemically or photochemically and contains surface-active agents.

U.S. Pat. No. 7,173,074 B2 describes chemically curable two-component resin-modified glass ionomer cements of the powder/liquid and paste/paste type.

US 2006/0030637 A1 proposes chemically curable two-component resin-modified glass ionomer cements to which photoinitiators can also be added. The cements can be of the powder/liquid, paste/liquid or paste/paste type. They are supposed, through the presence of salts, to exhibit better storage stabilities.

DE 10 2006 019 092 A1 concerns chemically curing two-component resin-modified glass ionomer cements of the paste/paste type.

US 2005/0252414 A1 proposes to improve, by the addition of a nanofiller, the esthetics of a resin-modified glass ionomer cement which can be cured chemically and/or photochemically. The refractive index of the liquid phase is supposed to be increased by the presence of the nanofiller and thus to lead to a better alignment of the refractive index of the matrix phase with the solid phase. This alignment is supposed to lead to the cured material exhibiting an improved optical translucency.

DE 602 09 714 T2 likewise describes resin-modified glass ionomer cements.

DE 195 26 224 B4 discloses resin-modified glass ionomer cements of the paste/paste and powder/liquid type which can be cured both chemically and photochemically. The systems are supposed to exhibit strongly improved physical properties, such as initial hardness, flexural strength and adhesive strength on dentin, in comparison to conventional glass ionomer cements. Light-cured cement compositions are supposed to be able to be selectively used for filling purposes and chemically curing compositions are supposed to be able to be selectively used for luting purposes.

U.S. Pat. No. 5,965,632 discloses resin reinforced glass ionomer cements of the paste/paste type.

The resin-modified glass ionomer cements described above exhibit, in comparison to the classical glass ionomer cements, some improved properties, such as compressive strength, flexural strength and solubility.

Of particular importance in a resin-modified glass ionomer cement is its initiator system for chemical curing. The special challenge within this context is based on the fact that resin-modified glass ionomer cements exhibit an acidic environment and a multitude of chemical substances from the redox systems are not stable in acids and lose their functionality. Within this context, aqueous acidic systems represent a very special challenge.

As a rule, the initiator system "benzoyl peroxide/aromatic tertiary amine" is used in dental chemistry for chemically curing masses. However, should this initiator system be used in the acidic environment as is present in resin-modified glass ionomer cements, the redox reactants fail to be effective. If the aromatic tertiary amine comes in contact with weak or strong acid functional groups, the compound is protonated and loses its ability to act as reducing agent. In addition, the benzoyl peroxide is readily decomposed under acidic conditions. These are the reasons why, for chemically curing dental compositions, the "Bredereck" systems were returned to quite early.

The classical "Bredereck system" had already been applied for in 1964 (DE 1495520), after extensive studies in the Bredereck working group on the redox-initiated cross-linking of unsaturated compounds in the 40s and 50s (U.S. Pat. Nos. 2,779,751, 2,776,952, 2,846,418, 2,935,489 and 2,894,932) had been successfully completed.

Since these beginnings, redox systems which are stable under acidic conditions have been ever more consistently extended.

DE 101 24 029 A1 discloses an initiator system for acidic dental formulations comprising a barbituric acid or thiobarbituric acid or a barbituric acid or thiobarbituric acid derivative, a peroxodisulfate compound and/or peroxodiphosphate compound, a sulfinic acid compound and a copper compound.

DE 197 57 277 A1 likewise describes a dental initiator system for the curing of acidic two-component masses. The initiator consists here of a copper salt, a sulfinic acid compound and a barbituric acid or thiobarbituric acid derivative. In this powder/liquid system, reducing and oxidizing agents are found in the powder component, while the copper salt is a constituent of the liquid phase.

DE 100 17 188 A1 claims two-component dental masses with a low setting temperature, wherein the component I comprises: a.) at least one vinyl ether, b.) at least one ethylenically unsaturated monomer which is not a vinyl ether, c.) at least one accelerator, d.) fillers, thixotropic auxiliaries and other auxiliaries, and component II comprises: e.) at least one barbituric acid derivative and/or malonyl sulfamide, which can initiate the radical polymerization, f.) optionally fillers, thixotropic auxiliaries, retarders and other auxiliaries, and also g.) common plasticizers.

The use of heavy metal compounds and in particular of copper complexes, and also ionogenically bonded halogens or pseudohalogens, such as organic ammonium chlorides, is provided for as accelerator according to constituent c.). In the examples, 1-benzyl-5-phenylbarbituric acid is used as reducing agent and (ß-phenylethyl)dibutylammonium chloride and bis(1-phenylpentane-1,3-dionato)copper(II) complex are used as accelerator in the paste/paste system. The reducing agent is part of the one paste, while heavy metal complex and ionogenic halogen compound are parts of the other paste. This composition according to the invention cures without peroxide.

DE 199 28 238 A1 provides a polymerizable dental mass which comprises a.) at least one ethylenically unsaturated monomer of double or higher functionality, b.) optionally at least one monofunctional ethylenically unsaturated monomer, c.) optionally an accelerator, d.) a redox initiator system which can initiate the radical polymerization, e.) optionally fillers, thixotropic auxiliaries, retarders and other auxiliaries, f.) a common plasticizer and is characterized in that the redox initiator system comprises a barbituric acid derivative and/or a malonyl sulfamide and an organic peroxide selected from the group of the mono- or polyfunctional carboxylic acid peroxyesters.

Here also, in the examples, 1-benzyl-5-phenylbarbituric acid is used as reducing agent and (ß-phenylethyl)dibutylammonium chloride and bis(1-phenylpentane-1,3-dionato)copper(II) complex are used as accelerator in the paste/paste system. 3,5,5-Trimethylhexanoic acid tert-butyl peroxyester can be added here to the reducing agent as oxidizing agent, without the system losing its stability. The ionogenic halogen compound and the heavy metal complex as parts of the redox system are constituents of the other paste. These dental masses are supposed to be suitable as filling materials, core build-up materials, luting cements and as temporary crown and bridge materials.

In order to achieve improved stabilities of the initiator systems, the corresponding salts have been used instead of the acids in the Bredereck systems. According to the old chemical rule that "the salt of a weak acid, on addition of a strong acid, gives the salt of the strong acid and the weak acid is released", storage-stable 1:1 paste/paste systems in particular should be obtained with this concept on the basis of CH acid compounds as initiators in chemically curing dental materials. The salts of CH acid compounds should be stable in the presence of polymerizable monomeric building blocks.

For this, examples are found in EP 1 872 767 A1, EP 2 070 506 A1, EP 2 055 324 A2, EP 2 198 824 A1, EP 0 923 924 A2, DE 11 2006 001 049 T5, EP 1 502 569 A1, EP 2 070 935 A1 or in EP 1 881 010 A1.

In spite of this large number of property right applications, there is to date, to our knowledge, no corresponding product on the market.

EP 1 269 968 A1 discloses a dental cement which comprises a.) a polymerizable monomer with acid group, b.) a polyalkenoic acid, c.) an ion-releasing filler, d.) a polymerizable monomer without acid functional group, e.) water, f.) a peroxide, g.) a salt of an aromatic sulfinic acid and h.) an aromatic secondary or tertiary amine. Oxidizing and reducing agents are separately present in these two-component systems, wherein the benzoyl peroxide has been formulated as oxidizing agent in the liquid aqueous phase together with the acidic polyacrylic acid. It is accordingly to be expected that the system exhibits no great storage stability.

US 2003/0166740 A1 likewise describes chemically curing two-component resin-modified glass ionomer cements in the powder/liquid and paste/paste form which can be applied without conditioning to the hard tooth structure. The palette of suitable reducing agents is here broadened by polymerizable urea and thiourea compounds. It is explained (cf. section [0077]) that, in such systems, reducing and oxidizing agents can be formulated in separate parts. They can be provided together in one part if the technology of microencapsulation is used (see also in this connection U.S. Pat. No. 5,154,762).

EP 2 371 346 A1 discloses a paste/paste system for tooth restoration which is supposed to exhibit particularly good storage stability. The redox system comprises a peroxide compound and an ascorbic acid compound.

WO 95/22955 A1 describes dental compositions of paste/paste type comprising ethylenically unsaturated functional groups with improved color stability. The compositions comprise an oxidizing agent and also metal-complexed ascorbic acid.

WO 2016/007453 A1 is directed at dental compositions and discloses a redox system comprising an ascorbic acid compound, a transition metal (preferably copper or iron) and organic peroxides (preferably hydroperoxides or diperoxides).

EP 2 712 888 A1 is targeted at dental curable formulations which can also be present in acidic anhydrous compositions. The redox system used here comprises an organic peroxide as oxidizing agent, a cysteine as reducing agent and also a polymerization accelerator. The latter can be copper compounds, for example copper sulfate, copper acetylacetonate, copper chloride, copper gluconate or copper oleate, or vanadium compounds, such as vanadium benzoylacetonate, vanadium naphthenate or vanadyl acetylacetonate.

EP 2 433 612 A1 claims resin-modified glass ionomer cement compositions which use, as redox system, the cysteine/sulfinic acid derivative combination.

The peroxide/thiourea combination is frequently disclosed, optionally in connection with a polymerization accelerator, as a rule an organic transition metal compound.

Thus, in EP 1 458 831 A2, a dental composition is disclosed which comprises a polymerizable reducing agent with an allylthiourea group (for example, 1-allylthiourea), an oxidizing agent (for example peroxide) and a secondary reducing agent (for example an amine, an ascorbic acid (derivative), a sulfinic acid (derivative) or a metal salt as redox system.

The system can also be a resin-modified glass ionomer cement and can be used in the form of a paste/paste, paste/liquid or powder/liquid system.

EP 2 233 544 A1 discloses a storage-stable resin-modified glass ionomer cement as paste/paste system which comprises a redox system based on a hydroperoxide, on a thiourea derivative and on a vanadium compound.

EP 1 754 465 A1 bears the title "2-Component initiator system (amine-free) with storage stability and particular suitability for acid systems". The redox initiator system of this amine-free composition comprises a hydroperoxide compound with one or more hydroperoxide groups which are bonded to a tertiary carbon, a thiourea derivative and also a copper compound which is soluble in the composition. The dental composition can be formulated as liquid/liquid, paste/paste, paste/liquid or powder/liquid system and is used for the preparation of a restorative orthodontically or endodontically usable preparation.

The document WO 95/22956 discloses a light-curable resin-modified glass ionomer cement in the paste/paste form. The glass ionomer cements disclosed can, in addition to the light curing, also be cured in other ways, namely in particular with the help of a redox catalyst system. WO 95/22956 discloses, in this respect, a list of preferred reducing agents which can be a constituent of the redox catalyst system (cf. page 19, first paragraph, and also claim 15).

A first object of the present invention was to make available a composition for use as component of a multicomponent resin-modified glass ionomer cement and also a corresponding multicomponent resin-modified glass ionomer cement which, in comparison with systems known from the state of the art, exhibit a higher storage stability and preferably also can be applied, after storage for several weeks, with setting times (also known as curing times) which at the most are insignificantly changed, to give cured dental materials which have good mechanical properties, in particular a high flexural strength.

In particular, the object of the present invention was to give a composition for use as component of a multicomponent resin-modified glass ionomer cement which, in comparison with corresponding compositions, which comprise, as reducing agent, one or more compounds (A) selected from the group consisting of the isomers of ascorbic acid, the salts of the isomers of ascorbic acid, the esters of the isomers of ascorbic acid and the ethers of the isomers of ascorbic acid, have an increased storage stability. The compounds (A) mentioned are to be exact admittedly widespread as effective and in practice particularly relevant constituents of redox initiator systems in components of resin-modified glass ionomer cements but disadvantageously regularly result in comparatively low storage stabilities of these components.

Apart from that, it was an additional object of the present invention to give a process for the manufacturing of such compositions to be given according to the invention. Additional (partial) objects of the present invention result from the enclosed patent claims and from the present description.

The abovementioned objects are achieved through compositions, multicomponent resin-modified glass ionomer cements, processes and uses as are defined in the enclosed claims. Preferred embodiments according to the invention result from the subclaims.

In particular, the present invention relates to a composition for use as component of a multicomponent resin-modified glass ionomer cement, the composition comprising
one or more radically polymerizable organic monomers (M)
and also, as constituent of a polymerization initiator system for it
one or more compounds (A) selected from the group consisting of the isomers of ascorbic acid, the salts of the isomers of ascorbic acid, the esters of the isomers of ascorbic acid and the ethers of the isomers of ascorbic acid
and
one or more compounds (S) selected from the group consisting of sulfinic acids, salts of sulfinic acids and salts of organoboron compounds.

The composition according to the invention comprises radically polymerizable organic monomers (M) and in addition a specific combination of compounds (A) and (S) which can act together as a reducing agent of a polymerization initiator system and together are responsible for a high storage stability of the composition according to the invention. The radically polymerizable organic monomers (M) present in the composition regularly already polymerize in the presence of many conventional reducing agents during the storage and accordingly already before the mixing of the polymerization initiator system with the oxidizing agent (as is usually present in an additional component of the multicomponent resin-modified glass ionomer cement).

It has been confirmed, in extensive separate studies, that the combination provided according to the invention of compound (A) and (S) as constituent of a polymerization initiator system, in comparison both with conventionally established and with earlier exotic initiator systems, surprisingly produces advantages with regard to the stability properties. The compositions according to the invention are not only, even after storage for several weeks, still surprisingly stable but can also then still be cured to give dental materials with surprisingly good mechanical properties, the setting time (curing time) being changed only to a comparatively small extent, in comparison to the compositions initially prepared.

Thus, the composition according to the invention proves to be, for example, as advantageous in comparison to compositions which, in addition to radically polymerizable organic monomers (M), comprise a tertiary amine, a sulfinate, a barbituric acid, a tertiary amine in combination with a sulfinate or a tertiary amine in combination with a borate.

This surprising discovery is in particular relevant for multicomponent resin-modified glass ionomer cements, the component of which comprising the reducing agent hitherto regularly has an unsatisfactory storage stability. The problem of the low storage stability and the need to be able to prepare dental materials with good mechanical properties, even from compositions stored for a long time, however also exists for other dental materials known to a person skilled in the art. The compositions according to the invention are accordingly, e.g., also relevant for such other multicomponent systems which are not glass ionomer cements but which are at least partially cured chemically, i.e. by means of a redox polymerization initiator system. Infiltrants, fissure sealants, dental lacquers, dental composite materials and dental compomer materials may be mentioned in particular within this context.

The "components" of a multicomponent resin-modified glass ionomer cement are present separately, i.e. separated in space, from the other component(s).

The expression "isomers of ascorbic acid" comprises L-ascorbic acid, D-ascorbic acid, L-isoascorbic acid and D-isoascorbic acid.

"Esters of the isomers of ascorbic acid" can be obtained by the reaction products of an isomer of ascorbic acid with an organic acid, in particular a linear or branched and saturated or unsaturated carboxylic acid with 2 to 26 carbon atoms.

"Ethers of the isomers of ascorbic acid" can be obtained by the reaction of an isomer of ascorbic acid with a halogenated hydrocarbon, in particular a linear or branched and saturated or unsaturated halogenated hydrocarbon with 1 to 26 carbon atoms.

Preference is given to a composition according to the invention additionally comprising a basic glass composition (G) as crosslinking agent for polymers containing carboxylic acid groups (P) selected from the group consisting of homo- and copolymers of an $\alpha,\beta$-unsaturated carboxylic acid (C).

Even if the constituents which are mentioned of the composition according to the invention in a multicomponent resin-modified glass ionomer cement do not inevitably have to be present in the same separate component as the basic glass composition (G), such a composition according to the invention is particularly preferred. It has been shown, in separate studies, that the presence of the basic glass composition in the composition according to the invention does not disadvantageously affect the storage stability and storage quality of the composition according to the invention. This discovery is particularly relevant for the conception of a resin-modified glass ionomer cement with merely two separate components; it makes possible a particularly convenient and simple handling and processing of the composition according to the invention and of a corresponding resin-modified glass ionomer cement altogether. For appropriate resin-modified glass ionomer cements according to the invention, reference may be made to the claims and the embodiments further below.

A person skilled in the art in the field of multicomponent resin-modified glass ionomer cements defines the basic glass composition usually functionally via its suitability or aptitude for crosslinking polymers containing carboxylic acid groups (P) selected from the group consisting of homo- and copolymers of an $\alpha,\beta$-unsaturated carboxylic acid (C) in the GIC setting. Correspondingly, the preferred composition according to the invention comprises a "basic glass composition (G) as crosslinking agent for polymers containing carboxylic acid groups (P) selected from the group consisting of homo- and copolymers of an $\alpha,\beta$-unsaturated carboxylic acid (C)"; the basic glass composition is thus suitable as crosslinking agent for these polymers. Within this context, the $\alpha,\beta$-unsaturated carboxylic acid (C) is preferably selected from the group consisting of acrylic acid, methacrylic acid, itaconic acid, fumaric acid, maleic acid, chloromethacrylic acid, cyanomethacrylic acid, aconitic acid, mesaconic acid, glutaconic acid and citraconic acid, is particularly preferably selected from the group consisting of acrylic acid and maleic acid.

Preference is given to a composition according to the invention (preferably as described above as preferred), wherein the basic glass composition (G) comprises one or more cations of elements which are selected from the group consisting of the metals of Main Groups I, II and III of the Periodic Table, are preferably selected from the group consisting of sodium, potassium, calcium and aluminum, and which are particularly preferably present in the form of one or more compounds selected from the group consisting of oxides, hydroxides, sulfates, nitrates, phosphates, carbonates, silicates, fluorides and nitrides. This means that the basic glass composition (G) preferably comprises, for example, potassium nitrate, sodium phosphate or aluminum fluoride. Corresponding basic glass compositions (G) are especially preferred because these acid-active elements can be relatively easily incorporated in glasses and such a basic glass composition in the GIC setting results in good mechanical properties.

With regard to the quantitative proportions to be used, reference is made to the statements in DE 39 41 629, DE 195 26 224 B4 and similar documents, in which it is also shown how the properties of the cured material depend on the type and amount of the acid-reactive elements (in particular on the metal cations mentioned) and their counterions. The release of the acid-reactive elements from the glass and thus the reactivity of the glass with regard to the acid functional groups is brought about by the targeted incorporation of defects in the lattice of the glass. This can, for example, be achieved by the variation in the amounts of trivalent cations used in comparison with $Si^{4+}$. Another possibility for the desired generation of lattice defects in the glass is represented by the use of fluoride ions since $F^-$, in comparison to $O^{2-}$, interferes with the construction of a regular lattice. Otherwise, the content of the acid-reactive elements in the glass is not specifically restricted.

Preference is given to a composition according to the invention (preferably as described above as preferred), wherein the basic glass composition (G) comprises an aluminum fluorosilicate glass.

Preferably, the basic glass composition (G) comprises an aluminum fluorosilicate glass since in practice particularly good mechanical properties for a correspondingly cured resin-modified glass ionomer cement can be obtained with this glass, while simultaneously the storage stability of a corresponding composition according to the invention (as separate component) is damaged exceptionally lightly. Main components of this glass are $Al^{3+}$, $Si^{4+}$, $F^-$, $O^{2-}$ and also $Ca^{2+}$ and/or $Sr^{2+}$ ions. The glass is produced according to the known processes. By way of example, silicon dioxide, aluminum oxide, aluminum hydroxide, aluminum silicate, strontium silicate, sodium fluoride, aluminum fluoride, aluminum phosphate, sodium aluminum fluoride and strontium phosphate are used as starting materials. The raw material is mixed and melted at over 1000° C., cooled, milled and separated according to particle size fractions.

Preference is given to a composition according to the invention (preferably as described above as preferred), wherein the basic glass composition (G) comprises one or more glasses with organically modified surface, preferably with silanized surface.

Preferably, the surface of one or more glasses in the basic glass composition (G) can be organically modified. The compatibility of the reactive glass powder with the other constituents of the composition is improved by a suitable modification. An organic surface modification of one, several or all glasses in the basic glass composition (G) should not, however, hinder the release of the reactive elements. Preference is given, for the case of a surface modification, to carrying out a silanization. Within this context, the surface of the reactive glass powder is, for example, coated with an organic silane compound which has a polymerizable ethylenically unsaturated double bond. Vinyltrimethoxysilane or in particular methacryloyloxypropyltrialkoxysilane is preferably used. The organosilane compounds can be used alone or in mixtures. Additional examples comprise silanes which exhibit no ethylenically unsaturated double bond, such as γ-aminopropyltrialkoxysilane, propyltrialkoxysilane, and the like.

Other surface-modifying agents can be fatty acids, organic acids, surfactants, inorganic acids, polysiloxanes, and the like.

To summarize, preference is given to a composition according to the invention (preferably as described above as preferred),
wherein the basic glass composition (G) comprises one or more cations of elements which are selected from the group consisting of the metals of Main Groups I, II and III of the Periodic Table, are preferably selected from the group consisting of sodium, potassium, calcium and aluminum,
    and which are particularly preferably present in the form of one or more compounds selected from the group consisting of oxides, hydroxides, sulfates, nitrates, phosphates, carbonates, silicates, fluorides and nitrides
and/or
    wherein the basic glass composition (G) comprises an aluminum fluorosilicate glass
and/or
    wherein the basic glass composition (G) comprises one or more glasses with organically modified surface, preferably with silanized surface.

Preference is given to a composition according to the invention (preferably as described above as preferred), additionally comprising one or more compounds (Z) selected from the group consisting of barbituric acids, tertiary amines and secondary amines.

In comparison with compositions which comprise simply one or more compounds (Z) as reducing agent, it has surprisingly been shown that the storage stability of compositions according to the invention which, at the same total molar amount of the reducing agent, also comprise the compounds (A) and (S), in addition to one or more compounds (Z), is improved. This is particularly advantageous because, by means of the compounds (Z), the curing kinetics of a resin-modified glass ionomer cement according to the invention can be brought into line particularly well with the respective requirements. In particular, the compounds (Z) are regularly used as "accelerators" for light-curing initiator systems in combination with photoinitiators, i.e. in combination with catalysts which act photosensitizing.

Preference is given to a composition according to the invention (preferably as described above as preferred), additionally comprising one or more photoinitiators, wherein the one or more photoinitiators are preferably selected from the group consisting of benzoin alkyl ethers, benzoin alkyl esters, benzil monoketals, acylphosphine oxides, benzophenones, acetophenones, ketals, thioxanthones, titanocenes, aliphatic 1,2-diketo compounds and aromatic 1,2-diketo compounds, are particularly preferably selected from the group comprising 2,2-diethoxyacetophenone, 9,10-phenanthrenequinone, diacetyl, furil, anisil, 4,4'-dichlorobenzil and 4,4'-dialkoxybenzil and camphorquinone.

Appropriate compositions according to the invention are in particular accordingly preferred because, for these compositions, in addition to the chemical curing, an additional curing mechanism is available with which the composition can optionally be cured even alone, i.e. without the mixing with an additional component. It is particularly advantageous that the presence of a photoinitiator does not negatively affect the storage stability of the composition according to the invention if this is stored with the exclusion of light; accordingly, an inconvenient and undesirable interaction between the compounds (A) and (S) with the photoinitiator thus does not occur. It is advantageous that the compounds (A) and (S) can act synergistically as accelerators for the photoinitiators and can accordingly increase the effectiveness of the photoinitiators preferably present in the composition according to the invention.

Preference is given to a composition according to the invention (preferably as described above as preferred), additionally comprising one or more inhibitors, wherein the one or more inhibitors are preferably selected from the group consisting of substituted phenols, phenothiazine, stable organic radicals and hydroquinone monomethyl ether, are particularly preferably selected from the group consisting of 2,6-di(tert-butyl)-4-methylphenol, hydroquinone monomethyl ether, the 2,2-diphenyl-1-picrylhydrazyl radical, the galvinoxyl radical, the triphenylmethyl radical and the 2,2, 6,6-tetramethylpiperidinyl-1-oxyl radical.

The inhibitors preferably used are suitable for preventing a premature radical polymerization of the radically polymerizable organic monomers (M). The inhibitors accordingly act in supporting the same technical effect which is achieved with compositions according to the invention. It is advantageous within this context for the effect of the inhibitors in compositions according to the invention not to be reduced, but the technical effect of the present invention is additive with the effect of the inhibitors. Accordingly, particularly advantageous and particularly storage-stable compositions can be manufactured. In particular, with the presence of photoinitiators in the composition according to the invention, the use of inhibitors allows the storage stability of the composition to be further increased.

Preference is given to a composition according to the invention (preferably as described above as preferred), additionally comprising one or more additives selected from the group consisting of colorants, tartaric acid, silica, stabilizers, modifiers, bactericidal substances and inert fillers.

The compositions according to the invention can comprise, as colorant, for example inorganic or organic pigments or dyes. Examples of this are given in DE 196 05 272.

The compositions according to the invention can comprise tartaric acid, in particular (+)tartaric acid. In resin-modified glass ionomer cements, tartaric acid is a suitable means for the control of the setting reaction between the basic glass composition (G) and the polymer containing carboxylic acid groups (P), which lengthens the working time; the setting rate, however, simultaneously accelerates.

The compositions according to the invention, in particular those which comprise a basic glass composition (G) and are present as paste, can comprise modifiers which contribute, in particular in the manufacturing of the composition, to the different constituents being able to be very satisfactorily processed to give a paste. Use may be made, as advantageous modifiers, for example, of water-soluble substances of high molecular weight, such as starch derivatives, carboxyalkylcelluloses, polyvinyl alcohol, polyethylene glycol, polyacrylamide, polyvinylpyrrolidone, xanthan gum, alginate, and the like. Through the use of (advantageous) modifiers, the rheological properties of compositions according to the invention (in particular pastes) can be precisely adjusted and can be brought into line with the respective practical requirements, without the storage stability being negatively affected. A similar purpose is fulfilled by the stabilizers, these for example being surfactants.

The composition according to the invention advantageously comprises bactericidal substances. Such substances, which are familiar to a person skilled in the art and commercially available, advantageously do not interfere with the technical effect observed for compositions according to the invention, but on the contrary increase the stability of compositions according to the invention to biological determinants which could reduce the storage stability.

The composition according to the invention, in particular a composition comprising a basic glass composition (G), preferably comprises known inorganic fillers which are used to a wide extent in dental composite materials and which are well known to a person skilled in the art. These are, for example, barium aluminum borosilicate glasses of different particle sizes which do not (like the basic glass composition (G)) react with a polymer containing carboxylic acid groups (P) selected from the group consisting of homo- and copolymers of an $\alpha,\beta$-unsaturated carboxylic acid (C). Such glasses can therefore be described as inert inorganic fillers. Quartz, feldspar, titanium dioxide and/or barium sulfate can also preferably be used as inert inorganic fillers. It is an advantage with these inert inorganic fillers that the solids content of the composition can be increased without the kinetics of the GIC setting being significantly affected. In addition, it is possible, with the inert inorganic fillers, to adjust the mechanical properties of the materials which can be obtained by curing the compositions according to the invention. Advantageously, the presence of inert inorganic fillers does not disadvantageously affect the storage stability of compositions according to the invention.

The use of silica, in particular of nanoscale nonagglomerated silica particles with a particle size of 1 to 200 nm, originating from the sol-gel process, leads to a still better space filling of the filler, so that the properties of the materials resulting by curing the compositions according to the invention become still more advantageous, in comparison with the products from the state of the art. Nanoscale nonagglomerated sols are commercially available in a broad range. Preferably, fillers of a particular geometry, which are obtained, for example, by spray drying of sols, can also be used. Examples of this are aggregated silica particles in the form of tori, such as are described in WO 00/25729 or in DE 102 53 481. Additional examples of suitable silicas are Aerosils, such as Aerosil 200, Aerosil OX 50, Aerosil R 972, Aerosil R 974, Aerosil R 8200, Aerosil R 711, Aerosil DT 4, and the like. Aluminum oxide C and also titanium dioxide P 25 also belong to the Aerosils. In addition, organic and/or organic/inorganic hybrid fillers can be used.

The inert inorganic fillers and/or the silica particles can preferably be surface modified, as is described above for the glasses of the basic glass composition.

To summarize, preference is accordingly given to a composition according to the invention (preferably as described above as preferred),
   additionally comprising one or more compounds (Z)
      selected from the group consisting of barbituric acids,
      tertiary amines and secondary amines
and/or
   additionally comprising one or more photoinitiators,
      wherein the one or more photoinitiators are preferably selected from the group consisting of benzoin alkyl ethers, benzoin alkyl esters, benzil monoketals, acylphosphine oxides, benzophenones, acetophenones, ketals, thioxanthones, titanocenes, aliphatic 1,2-diketo compounds and aromatic 1,2-diketo compounds, are particularly preferably selected from the group comprising 2,2-diethoxyacetophenone, 9,10-phenanthrenequinone, diacetyl, furil, anisil, 4,4'-dichlorobenzil and 4,4'-dialkoxybenzil and camphorquinone and/or
additionally comprising one or more inhibitors,
wherein the one or more inhibitors are preferably selected from the group consisting of substituted phenols, phenothiazine, stable organic radicals and hydroquinone monomethyl ether, are particularly preferably selected from the group consisting of 2,6-di(tert-butyl)-4-methylphenol, hydroquinone monomethyl ether, the 2,2-diphenyl-1-picrylhydrazyl radical, the galvinoxyl radical, the triphenylmethyl radical and the 2,2,6,6-tetramethylpiperidinyl-1-oxyl radical and/or
additionally comprising one or more additives selected from the group consisting of colorants, tartaric acid, silica, stabilizers, modifiers, bactericidal substances and inert fillers.

Preference is given to a composition according to the invention (preferably as described above as preferred), wherein the one or at least one of the several radically polymerizable organic monomers (M)
is selected from the group consisting of monomers with at least two ethylenic groups (M1),
wherein the monomers with at least two ethylenic groups (M1) are preferably selected from the group consisting of diacrylates, triacrylates, dimethacrylates, trimethacrylates, are particularly preferably selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, glycerol 1,3-dimethacrylate, tetraethylene glycol dimethacrylate, neopentyl glycol dimethacrylate, 2,2-bis[4-[3-methacryloyloxy-2-hydroxypropoxy]phenyl]propane and the di(meth)acrylates of dihydroxymethyltricyclo[5.2.1.0$^{2,6}$]decane and/or
wherein the one or at least one of the several or at least one additional of the several radically polymerizable organic monomers (M)
is selected from the group consisting of hydroxyl compounds with at least one ethylenic group (M2),
wherein the hydroxyl compounds with at least one ethylenic group (M2) are preferably selected from the group consisting of 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate and 2,2-bis[4-[3-methacryloyloxy-2-hydroxypropoxy]phenyl]propane.

This means, for the case of the "or" linkage, that the one or at least one of the several radically polymerizable organic monomers (M) is selected from the group consisting of monomers with at least two ethylenic groups (M1) and hydroxyl compounds with at least one ethylenic group (M2).

Accordingly, in this case, the one or at least one of the several radically polymerizable organic monomers (M) is preferably selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, tetraethylene glycol dimethacrylate, neopentyl glycol dimethacrylate and the di(meth)acrylates of dihydroxymethyltricyclo [5.2.1.0$^{2,6}$]decane, 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate and 2,2-bis[4-[3-methacryloyloxy-2-hydroxypropoxy]phenyl]propane.

Very particularly preferred are those compositions according to the invention in which all of the radically polymerizable organic monomers (M) are selected from the above list.

Such compositions according to the invention are preferred because the corresponding radically polymerizable organic monomers (M) in practice show a particular compatibility with the compounds (A) and (S) and particularly storage-stable compositions can be obtained with these monomers. In addition, corresponding radically polymerizable organic monomers (M) with a polymerization initiator system comprising the compounds (A) and (S) can be particularly efficiently polymerized, without chemical incompatibilities occurring. Accordingly, corresponding compositions according to the invention advantageously lead, after the curing, to (according to the invention, see the claims and the embodiments further below) cured dental materials with particularly good mechanical properties.

The above definition of a preferred embodiment of a composition according to the invention means, for the case of the "and" linkage, which is preferred in comparison with the "or" linkage described above, that at least one of the several radically polymerizable organic monomers (M) is selected from the group consisting of monomers with at least two ethylenic groups (M1) or the correspondingly preferred list and at least one of the several radically polymerizable organic monomers (M) is selected from the group consisting of hydroxyl compounds with at least one ethylenic group (M2) or the correspondingly preferred list.

While certain monomers meet both characteristics, namely the hydroxyl compounds with at least two ethylenic groups, such as, e.g., 2,2-bis[4-[3-methacryloyloxy-2-hydroxypropoxy]phenyl]propane, it is preferable for at least one of the radically polymerizable organic monomers (M) to be selected from the group consisting of monomers with at least two ethylenic groups (M1) or the correspondingly preferred list and for at least one other of the radically polymerizable organic monomers (M) to be selected from the group consisting of hydroxyl compounds with at least one ethylenic group (M2) or the correspondingly preferred list, with the proviso that the compounds selected are different radically polymerizable organic monomers (M). Very particularly preferred within this context are those compositions according to the invention in which all of the radically polymerizable organic monomers (M) are selected from the group consisting of monomers with at least two ethylenic groups (M1) and hydroxyl compounds with at least one ethylenic group (M2), or the correspondingly preferred lists.

Such compositions according to the invention are first in turn preferred because the corresponding radically polymerizable organic monomers (M) of the groups (M1) and (M2) in practice show a particular compatibility with the compounds (A) and (S) and particularly storage-stable compositions can be obtained with these monomers.

In addition, such preferred compositions according to the invention with two different radically polymerizable organic monomers (M), at least one of which is selected from the group consisting of monomers with at least two ethylenic groups (M1) and at least one of which is selected from the group consisting of hydroxyl compounds with at least one ethylenic group (M2), or the correspondingly preferred lists, exhibit superior curing kinetics and can still be cured, even after storage for several weeks, to give dental materials with good mechanical properties. Within this context, it has surprisingly been found that the setting time (curing time) of such preferred compositions according to the invention is particularly little influenced by the storage.

In addition to the monomers with at least two ethylenic groups (M1) already described above as preferred, the patent literature mentions a multitude of additional compounds which are, all of them, diesters of acrylic or methacrylic acid and are suitable for use in a composition according to the invention. Use may preferably be made of the corresponding dimethacrylates or diacrylates of dihydroxymethyltricyclo [$5.2.1.0^{2,6}$]decane, such as described in the publications DE 2816823, DE 2419887, DE 2406557, DE 2931926, DE 3522005, DE 3522006, DE 3703120, DE 102005021322, DE 102005053775, DE 102006060983, DE 69935794 and DE 102007034457.

Preference is given to a composition according to the invention (preferably as described above as preferred), wherein the one or at least one of the several compounds (A) is selected from the group consisting of ascorbic acid, salts of ascorbic acid, isoascorbic acid and salts of isoascorbic acid, is preferably selected from the group consisting of ascorbic acid, sodium ascorbate, isoascorbic acid and sodium isoascorbate
and/or
wherein the one or at least one of the several compounds (S) is selected from the group consisting of aromatic sulfinic acids, salts of aromatic sulfinic acids and salts of aromatic organoboron compounds, is preferably selected from the group consisting of toluenesulfinic acid, sodium toluenesulfinate, potassium toluenesulfinate, benzenesulfinic acid, sodium benzenesulfinate, potassium benzenesulfinate, sodium tetraphenylborate and lithium tetraphenylborate, is particularly preferably selected from the group consisting of toluenesulfinic acid, sodium toluenesulfinate, potassium toluenesulfinate, benzenesulfinic acid, sodium benzenesulfinate and potassium benzenesulfinate.

Particularly high storage stabilities and also a favorable setting behavior, i.e. setting times (curing times) which are as unchanged as possible, even after storage for several weeks, are achieved for such preferred compositions according to the invention. The compounds (A) defined above are within this context particularly effective and high-performance reducing agents, for which a particularly advantageous effect in combination with the compounds (S) has been shown in separate tests, wherein the compounds (S) defined above, which alone are frequently not regarded as satisfactorily high-performance reducing agents, showed a particularly pronounced technical effect on mixing with the compounds (A).

This technical effect consists, as explained above, in particular in that the combination of the compounds (A) and (S) leads to a constituent of a polymerization initiator system in a composition according to the invention which has a high performance but synergistically induces a premature polymerization of the radically polymerizable organic monomers (M) present in the composition less strongly than is done by a comparative constituent of a polymerization initiator system of a composition not according to the invention, which contains simply the compound (A) (in equal total molar amount).

Particular preference is given to a composition according to the invention (preferably as described above as preferred), wherein the compound (A) is selected from the group consisting of ascorbic acid, sodium ascorbate, isoascorbic acid and sodium isoascorbate and the compound (S) is selected from the group consisting of toluenesulfinic acid, sodium toluenesulfinate, potassium toluenesulfinate, benzenesulfinic acid, sodium benzenesulfinate, potassium benzenesulfinate, sodium tetraphenylborate and lithium tetraphenylborate, is particularly preferably selected from the group consisting of toluenesulfinic acid, sodium toluenesulfinate, potassium toluenesulfinate, benzenesulfinic acid, sodium benzenesulfinate and potassium benzenesulfinate.

Particular preference is given to a composition according to the invention (preferably as described above as preferred), wherein all of the compounds (A) are selected from the group consisting of ascorbic acid, sodium ascorbate, isoascorbic acid and sodium isoascorbate and all of the compounds (S) are selected from the group consisting of toluenesulfinic acid, sodium toluenesulfinate, potassium toluenesulfinate, benzenesulfinic acid, sodium benzenesulfinate and potassium benzenesulfinate.

The most advantageous storage stabilities are observed for such preferred compositions according to the invention.

Preference is given to a composition according to the invention (preferably as described above as preferred), wherein the ratio of the total molar amount of all of the compounds (A) to the total molar amount of all of the compounds (S)
is greater than 0.2, preferably greater than 0.3, particularly preferably greater than 1
and/or
is in the range from 0.2 to 50, preferably in the range from 0.3 to 20, particularly preferably in the range from 1 to 10.

The result, in such preferred compositions according to invention, is a particularly pronounced advantageous effect of the combination of the compounds (A) and (S) for the storage stability of the composition according to the invention and on the mechanical properties of the dental material which can be prepared from the composition by curing.

Preference is given to a composition according to the invention (preferably as described above as preferred), wherein the ratio of the combined total weight of all of the compounds (A) and all of the compounds (S) to the total weight of all of the radically polymerizable organic monomers (M) lies in the range from 0.05 to 10% by weight, preferably in the range from 0.5 to 7% by weight
and/or
wherein the total content of radically polymerizable organic monomers (M) lies in the range from 15 to 95% by weight, preferably in the range from 25 to 40% by weight, based on the total weight of the composition
and/or
wherein the combined total content of all of the compounds (A) and all of the compounds (S) lies in the range from 0.05 to 7% by weight, preferably in the range from 0.1 to 2.5% by weight, based on the total weight of the composition.

Each of the above compositions according to the invention is preferred since the technical effect can be best observed and measured for the defined ratios by weight or with the total contents given.

With very low contents of reducing agent, significant differences from conventional systems, for example, only appear after relatively long storage times, whereas particularly large contents of reducing agent (and in particular of compounds (A)) can lead, even in compositions according to the invention, to a really fast polymerization, which is not always acceptable. Very appropriately, the surprising technical effects are then particularly pronounced if the total content of radically polymerizable organic monomers (M) exceeds a certain minimum value, since a concentration of the monomers (M) which is too low slows down the polymerization kinetics.

Preference is given to a composition according to the invention (preferably as described above as preferred), wherein the composition
 is liquid or a paste
 and
 after storing at 37° C. for 6 weeks, preferably 8 weeks, particularly preferably 10 weeks and very particularly preferably 12 weeks, has a viscosity which is smaller than 10 000 Pa·s, is preferably smaller than 8000 Pa·s
and/or
wherein the composition exhibits, directly after the manufacturing, a viscosity which is smaller at the most by the factor 5, preferably at the most by the factor 3, than the viscosity of the corresponding component after storing at 37° C. for 6 weeks.

The negative effect of reducing agents (in particular compounds (A)) on the storage stability regularly appears at the clearest in liquids or pastes, so that the biggest absolutely achievable improvements in the storage stability can be observed for them too. The preferred compositions according to the invention defined above are particularly advantageous because they can still be applied very well even after 6 weeks of storage at 37° C. and in this respect are still sufficiently similar for practical purposes to the corresponding compositions directly after manufacturing.

The viscosity is determined (if not otherwise indicated) by means of a rheometer (Physica MCR 301) from Anton Paar (Graz, Austria). The measurement is carried out at 23° C. (at an ambient pressure of 1 bar) in the rotational test with plate/plate arrangement (diameter 25 mm, gap 1 mm). The viscosity is measured for three shear rates of 10 s$^{-1}$ (15 s), 1 s$^{-1}$ (30 s) and 0.1 s$^{-1}$ (60 s). Within this context, the value in brackets gives the time interval. 1 measured value per shear rate is recorded. 3 measured values in a range from 0.1 to 10 s$^{-1}$ are thus available. The value which is measured at a shear rate of 0.1 s$^{-1}$ is given as viscosity. The measurement is carried out as described (from high to low shear rate); accordingly, an always equal preshearing of the material is guaranteed. At low shear rates in particular, the preshearing would, by the application of the material to the measurement plate and the driving together of the measuring plates, otherwise be higher than the shearing during the measurement and the measurement accordingly would scarcely be reproducible.

Preference is given to a composition according to the invention (preferably as described above as preferred), comprising
 0.01 to 5% by weight, preferably 0.05 to 1% by weight, of one or more compounds selected from the group consisting of ascorbic acid, sodium ascorbate, isoascorbic acid and sodium isoascorbate,
 0.01 to 5% by weight, preferably 0.05 to 1% by weight, of one or more compounds selected from the group consisting of toluenesulfinic acid, sodium toluenesulfinate, potassium toluenesulfinate, benzenesulfinic acid, sodium benzenesulfinate, potassium benzenesulfinate, sodium tetraphenylborate and lithium tetraphenylborate,
 2 to 40% by weight, preferably 3 to 30% by weight, of one or more compounds selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, glycerol 1,3-dimethacrylate, tetraethylene glycol dimethacrylate, neopentyl glycol dimethacrylate, 2,2-bis[4-[3-methacryloyloxy-2-hydroxypropoxy]phenyl]propane and the di(meth)acrylates of dihydroxymethyltricyclo[5.2.1.0$^{2,6}$]decane,
 3 to 60% by weight, preferably 6 to 40% by weight, of one or more compounds selected from the group consisting of 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate, 2,2-bis[4-[3-methacryloyloxy-2-hydroxypropoxy]phenyl]propane,
and
 5 to 85% by weight, preferably 20 to 80% by weight, of aluminum fluorosilicate glass,
wherein the percentage values are based on the total weight of the composition.

Such preferred compositions have proven to be particularly advantageous in practical tests because they have a particularly high storage stability and their properties are changed only to a relatively slight extent even after storage for several weeks at 37° C. If corresponding compositions according to the invention are used as component of a multicomponent resin-modified glass ionomer cement, a cured resin-modified glass ionomer cement can even be obtained after storage for several weeks at 37° C. by mixing the components, the mechanical properties of which, in particular the flexural strength of which, are only insignificantly influenced by the preceding storage of the separate components.

Preference is given to a composition according to the invention (preferably as described above as preferred), comprising
 ascorbic acid and/or sodium isoascorbate in a total amount of 0.1 to 1% by weight,
 sodium toluenesulfinate and/or sodium tetraphenylborate in a total amount of 0.01 to 1% by weight,
 urethane dimethacrylate and/or triethylene glycol dimethacrylate and/or glycerol 1,3-dimethacrylate in a total amount of 5 to 20% by weight,
 2-hydroxyethyl methacrylate and/or 2-hydroxypropyl methacrylate in a total amount of 10 to 30% by weight,
 0.01 to 1% by weight of 2,6-di(tert-butyl)hydroxytoluene and
 50 to 75% by weight of aluminum fluorosilicate glass,
wherein the percentage values are based on the total weight of the composition.

For such preferred compositions, the most advantageous overall properties could be achieved in separate tests. In particular, the substances selected for the compounds (A) and (S) and also for the radically polymerizable organic monomers (M) and the basic glass composition (G) were within this context iteratively matched with and adapted to one another in comprehensive development stages. For the preferred compositions, the high storage stability of the composition according to the invention with particularly favorable application properties and a high performance of the cured resin-modified glass ionomer cement prepared are combined.

Preference is given to a composition according to the invention (preferably as described above as preferred), the composition being anhydrous
and/or
the composition not comprising any polymer containing carboxylic acid groups (P) selected from the group consisting of homo- and copolymers of an α,β-unsaturated carboxylic acid (C)
and/or
the composition not comprising any oxidizing agent (O) selected from the group consisting of persulfates, permanganates, perborates, peroxides and hydroperoxides.

Such compositions according to the invention are accordingly particularly preferred because the storage stability and/or the ability to cure of compositions according to the invention in the preferred absence of the constituents defined above are regularly better than in their presence. The compounds (A) and (S) are, e.g., regularly not particularly stable in aqueous and/or acidic compositions. The presence of an oxidizing agent (O) in the composition according to the invention could, in the presence of the compounds (A) and/or (S), initiate the polymerization of the radically polymerizable organic monomers (M) and is accordingly undesirable. As the composition according to the invention also comprises a basic glass composition (G), the simultaneous presence of a polymer containing carboxylic acid groups (P) would likewise result in the direct curing of the composition through GIC setting.

A person skilled in the art knows that, in compositions according to the invention, for example partially by impurities of starting materials, by atmospheric moisture or by material residues on the manufacturing equipment used, in individual cases quite small amounts of the preceding substances may be present, even if this is undesirable. Generally, in this case, the influence of these impurities, however, can be ignored or is still acceptable.

For the abovementioned reasons, preference is accordingly also given to a composition according to the invention (preferably as described above as preferred),
comprising less than 0.5% by weight, preferably less than 0.01% by weight, of water
and/or
comprising less than 0.5% by weight, preferably less than 0.01% by weight, of polymers containing carboxylic acid groups (P)
and/or
comprising less than 0.5% by weight, preferably less than 0.01% by weight, of oxidizing agents (O) selected from the group consisting of persulfates, permanganates, perborates, peroxides and hydroperoxides,
wherein the percentage values are based on the total weight of the composition.

The present invention also relates, according to an additional aspect, to a multicomponent resin-modified glass ionomer cement comprising a composition according to the invention as first component (the preceding statements on preferred embodiments are valid in this respect)
and
in one or more additional components, at least
one or more polymers containing carboxylic acid groups (P) selected from the group consisting of homo- and copolymers of an α,β-unsaturated carboxylic acid (C),
water
and
one or more oxidizing agents (O) selected from the group consisting of persulfates, permanganates, perborates, peroxides and hydroperoxides,
the multicomponent resin-modified glass ionomer cement comprising, in the first and/or an additional component, a basic glass composition (G) as crosslinking agent for the polymers (P),
with the proviso that the basic glass composition (G) is not present in a component together with a polymer containing carboxylic acid groups (P) and/or together with water.

Such a multicomponent resin-modified glass ionomer cement is to be understood as kit. The kit according to the invention comprises two, three or more separate components, i.e. components which are present segregated from one another in space; preferably, it consists of two separate components. The kit according to the invention has a high storage stability and can be cured, even after storage for several weeks, by mixing the components, to give a cured resin-modified glass ionomer cement, the mechanical properties of which are only insignificantly influenced by the preceding storage.

A person skilled in the art accordingly understands that a multicomponent resin-modified glass ionomer cement is preferred, comprising
a composition according to the invention as first component
and
in one or more additional components, at least
one or more polymers containing carboxylic acid groups (P) selected from the group consisting of homo- and copolymers of an α,β-unsaturated carboxylic acid (C),
water
and
one or more oxidizing agents (O) selected from the group consisting of persulfates, permanganates, perborates, peroxides and hydroperoxides,
the multicomponent resin-modified glass ionomer cement comprising, in the first and/or an additional component, a basic glass composition (G) as crosslinking agent for the polymers (P),
wherein the basic glass composition (G) and the polymer containing carboxylic acid groups (P) are present in separate components
and/or
wherein the basic glass composition (G) and the water are present in separate components.

Preferably, in a multicomponent resin-modified glass ionomer cement according to the invention, all of the compounds (A) and (S) are present only in the first component, the one or the several radically polymerizable organic monomers (M) being present in the first component and at least one additional component.

The multicomponent resin-modified glass ionomer cements according to the invention described above are in particular therefore particularly storage stable because, first, a composition according to the invention is used as component and because, secondly, the effects of chemical incompatibilities are avoided.

Preferably, the water and the polymer containing carboxylic acid groups (P) should not be present in the same component as the composition according to the invention, i.e. the water and the polymer containing carboxylic acid groups (P) should be present exclusively in the additional components. Were water and/or the polymer containing carboxylic acid groups (P) present in the same component as the composition according to the invention, then the compounds (A) and (S) would possibly not be sufficiently stable.

Preferably, the oxidizing agent (O) should not be present in the same component as the composition according to the invention, i.e. the oxidizing agent (O) should be present exclusively in the additional components. If the oxidizing agent (O) were a constituent of the same component as the composition according to the invention, an unintentional polymerization of the radically polymerizable organic monomers (M) could occur by the interaction with the compounds (A) and (S).

If the basic glass composition (G) and the polymer containing carboxylic acid groups (P) were constituents of the same component, unintentional curing might occur by the GIC setting.

If the basic glass composition (G) and the water were constituents of the same component, a disadvantageous reaction between water and the constituents of the glass could at least partly occur, which could result in a reduced ability of the glass to react as crosslinking agent for polymers containing carboxylic acid groups (P) selected from the group consisting of homo- and copolymers of an α,β-unsaturated carboxylic acid (C).

Polymers containing carboxylic acid groups (P) selected from the group consisting of homo- and copolymers of an α,β-unsaturated carboxylic acid (C) result, e.g., after a radical polymerization of, for example, an aqueous α,β-unsaturated acrylic, methacrylic, itaconic, fumaric, maleic, chloromethacrylic, cyanomethacrylic, aconitic, mesaconic, glutaconic or citraconic acid, and the like. If organic α,β-unsaturated mono- or dicarboxylic acids (or the anhydrides thereof) are polymerized individually, homopolymers are thus obtained. If the polymerization is carried out in the presence of two or more acids, copolymers are thus attained. Only one (homo- or co)polymer or a mixture of different polymers can be used according to the invention.

The α,β-unsaturated carboxylic acids (C) (which are used for the synthesis of the polymer containing carboxylic acid groups (P)) are structurally not particularly limited and can be used independently of the number of carboxylic acid groups in the molecule or of the presence of a carboxylic acid anhydride group or of other substituents.

The homo- or copolymers or the mixtures can be used in the form of their aqueous solutions.

Water can be used demineralized or also simply as faucet water.

The kit according to the invention can exist as a two-component kit in the paste/liquid form or, very particularly preferably, as paste/paste.

Preference is given to a multicomponent resin-modified glass ionomer cement according to the invention (preferably as described above as preferred),
wherein the α,β-unsaturated carboxylic acid (C) (which is used for the synthesis of the polymer containing carboxylic acid groups (P)) is selected from the group consisting of acrylic acid, methacrylic acid, itaconic acid, fumaric acid, maleic acid, chloromethacrylic acid, cyanomethacrylic acid, aconitic acid, mesaconic acid, glutaconic acid and citraconic acid, is preferably selected from the group consisting of acrylic acid and maleic acid
and/or
wherein the weight-average molecular weight $M_w$ of the total amount of the polymers containing carboxylic acid groups (P) lies in the range from 1000 to 150 000 g/mol, preferably between 40 000 and 100 000 g/mol.

Corresponding multicomponent resin-modified glass ionomer cements according to the invention exhibit particularly good curing kinetics and result, after the curing, in cured resin-modified glass ionomer cements with particularly advantageous mechanical properties. It is very particularly advantageous that corresponding multicomponent resin-modified glass ionomer cements according to the invention can be applied particularly easily; in particular, their components can be easily mixed.

If the weight-average molecular weight $M_w$ of the total amount of the polymers containing carboxylic acid groups (P) is less than 1000 g/mol, in many cases the mechanical properties of the resulting dental formulations are unsatisfactory, the adhesion of the material to the tooth substance is poor and the patient is conscious of a bad taste and notices an unpleasant smell. If the weight-average molecular weight $M_w$ of the total amount of the polymers containing carboxylic acid groups (P) exceeds a value of 150 000 g/mol, the viscosity in many cases climbs so strongly that a homogeneous mixing of the components is made more difficult or even impossible.

Furthermore, it is possible to use the polymers containing carboxylic acid groups (P) in solid form. For this, the polymer solutions are, for example, freeze-dried or subjected to other suitable methods.

Preference is given to a multicomponent resin-modified glass ionomer cement according to the invention (preferably as described above as preferred),
wherein the basic glass composition (G) comprises one or more cations of elements which are selected from the group consisting of the metals of Main Groups I, II and III of the Periodic Table, are preferably selected from the group consisting of sodium, potassium, calcium and aluminum,
and which are particularly preferably present in the form of one or more compounds selected from the group consisting of oxides, hydroxides, sulfates, nitrates, phosphates, carbonates, silicates, fluorides and nitrides
and/or
wherein the basic glass composition (G) comprises an aluminum fluorosilicate glass
and/or
wherein the basic glass composition (G) comprises one or more glasses with organically modified surface, preferably with silanized surface.

The advantages correspondingly of multicomponent resin-modified glass ionomer cements according to the invention correspond to those which are explained previously for the preferred compositions according to the invention which comprise a basic glass composition (G).

Preference is given to a multicomponent resin-modified glass ionomer cement according to the invention (preferably as described above as preferred),
wherein the one or at least one of the several oxidizing agents (O) is selected from the group consisting of peroxides and hydroperoxides, is preferably selected from the group consisting of hydroperoxides.

Corresponding multicomponent resin-modified glass ionomer cements according to the invention are preferred because the stated preferred oxidizing agents have in practice proved to be particularly compatible with the compounds (A) and (S). This means that, by the mixing of corresponding oxidizing agents (O) with compositions according to the invention as constituents of multicomponent resin-modified glass ionomer cements, particularly favorable, i.e. as unchanged as possible, setting times are obtained, even after relatively long storage times.

Preference is given to a multicomponent resin-modified glass ionomer cement according to the invention (preferably as described above as preferred), additionally comprising, in the first and/or an additional component
one or more compounds (Z) selected from the group consisting of barbituric acids, tertiary amines and secondary amines
and/or
one or more photoinitiators,
wherein the one or more photoinitiators are preferably selected from the group consisting of benzoin alkyl ethers, benzoin alkyl esters, benzil monoketals, acylphosphine oxides, benzophenones, acetophenones, ketals, thioxanthones, titanocenes, aliphatic 1,2-diketo compounds and aromatic 1,2-diketo compounds, are preferably selected from the group comprising 2,2-diethoxyacetophenone, 9,10-phenanthrenequinone, diacetyl, furil, anisil, 4,4'-dichlorobenzil and 4,4'-dialkoxybenzil and camphorquinone
and/or
one or more inhibitors,
wherein the one or more inhibitors are preferably selected from the group consisting of substituted phenols, phenothiazine, stable organic radicals and hydroquinone monomethyl ether, are particularly preferably selected from the group consisting of 2,6-di(tert-butyl)-4-methylphenol, hydroquinone monomethyl ether, the 2,2-diphenyl-1-picrylhydrazyl radical, the galvinoxyl radical, the triphenylmethyl radical and the 2,2,6,6-tetramethylpiperidinyl-1-oxyl radical
and/or
one or more additives selected from the group consisting of colorants, tartaric acid, silica, stabilizers, modifiers, bactericidal substances and inert fillers.

The advantages of these preferred multicomponent resin-modified glass ionomer cements according to the invention correspond to those which are explained previously for the preferred compositions according to the invention and the ingredients thereof.

The invention relates, according to an additional aspect, to a process for the manufacturing of a composition according to the invention (as defined above, preferably as described above as preferred) or for the preparation of a cured dental material, wherein a composition according to the invention (as defined above, preferably as described above as preferred) is manufactured as intermediate, comprising the following stages:
stage (a) synthesis or provision of one or more radically polymerizable organic monomers (M),
stage (b) synthesis or provision of one or more compounds (A) selected from the group consisting of the isomers of ascorbic acid, the salts of the isomers of ascorbic acid, the esters of the isomers of ascorbic acid and the ethers of the isomers of ascorbic acid,
stage (c) synthesis or provision of one or more compounds (S) selected from the group consisting of sulfinic acids, salts of sulfinic acids and salts of organoboron compounds and
stage (d) after stages (a), (b) and (c), mixing of the monomers (M) with the compounds (A) and (S).

With regard to the substances (M), (A) and (S) used in stages (a) to (d), the remarks made previously concerning other aspects of the invention are correspondingly valid each time.

The stages (a), (b) and (c) have any sequence. Stage (d) can comprise substages, e.g. if a premixing of individual constituents is desired.

The process according to the invention can be carried out particularly easily with regard to equipment and a person skilled in the art has the possibility of carrying out the mixing in stage (d) by numerous different methods. The mixing of the monomers (M) with all of the compounds (A) and the mixing of the monomers (M) with all of the compounds (S) are preferably carried out simultaneously, i.e. not one after the other. Accordingly, the process preferably comprises, as constituent of stage (d), a (sub)stage whereby, in the (sub)stage, all of the compounds (A) and (S) are mixed with one another.

The term "cured dental material" describes, for use in the dental field, suitable compositions independently of the degree of the curing. Thus, as soon as, for example in a dental composition, the polymerization of monomers (M) (and accordingly a curing) has started, a cured dental material is present. This definition is necessary because an end point of a curing in dental materials cannot regularly be sharply defined and polymerization can still occur to a slight extent even in obviously cured materials. Taking the example of a multicomponent resin-modified glass ionomer cement according to the invention, this means that, immediately after the mixing of the components and accordingly after the beginning of the polymerization of the monomers (M) and also after the beginning of the GIC setting, a cured dental material is already present. Likewise, for example a processed glass ionomer cement, for example with which an implant is luted, is a cured dental material.

Preference is given to processes according to the invention (preferably as described above as preferred) in which preferred or particular preferred compositions according to the invention are manufactured, wherein the advantages of these processes each time result from the advantages disclosed above of the preferred compositions manufactured. Corresponding particularly preferred processes are disclosed below.

Preference is given to a process according to the invention (preferably as described above as preferred), wherein the one or at least one of the several radically polymerizable organic monomers (M)
is selected from the group consisting of monomers with at least two ethylenic groups (M1),
wherein the monomers with at least two ethylenic groups (M1) are preferably selected from the group consisting of diacrylates, triacrylates, dimethacrylates, trimethacrylates, are particularly preferably selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, glycerol 1,3-dimethacrylate, tetraethylene glycol dimethacrylate, neopentyl glycol dimethacrylate, 2,2-bis[4-[3-methacryloyloxy-2- hydroxypropoxy]phenyl]propane and the di(meth)acrylates of dihydroxymethyltricyclo[5.2.1.0$^{2,6}$]decane and/or wherein the one or at least one of the several or at least one additional of the several radically polymerizable organic monomers (M)

is selected from the group consisting of hydroxyl compounds with at least one ethylenic group (M2), wherein the hydroxyl compounds with at least one ethylenic group (M2) are preferably selected from the group consisting of 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-dimethacrylate and 2,2-bis[4-[3-methacryloyloxy-2-hydroxypropoxy]phenyl]propane.

Particularly preferred within this context is the "and" linkage. It is likewise preferred for all of the radically polymerizable organic monomers (M) to be selected from the group consisting of monomers with at least two ethylenic groups (M1) and hydroxyl compounds with at least one ethylenic group (M2).

Preference is given to a process according to the invention (preferably as described above as preferred), wherein the one or at least one of the several compounds (A) is selected from the group consisting of ascorbic acid, salts of ascorbic acid, isoascorbic acid and salts of isoascorbic acid, is preferably selected from the group consisting of ascorbic acid, sodium ascorbate, isoascorbic acid and sodium isoascorbate and/or wherein the one or at least one of the several compounds (S) is selected from the group consisting of aromatic sulfinic acids, salts of aromatic sulfinic acids and salts of aromatic organoboron compounds, is preferably selected from the group consisting of toluenesulfinic acid, sodium toluenesulfinate, potassium toluenesulfinate, benzenesulfinic acid, sodium benzenesulfinate, potassium benzenesulfinate, sodium tetraphenylborate and lithium tetraphenylborate, is particularly preferably selected from the group consisting of toluenesulfinic acid, sodium toluenesulfinate, potassium toluenesulfinate, benzenesulfinic acid, sodium benzenesulfinate and potassium benzenesulfinate.

Preference is given to a process according to the invention (preferably as described above as preferred), wherein the ratio of the total molar amount of all of the compounds (A) to the total molar amount of all of the compounds (S)

is greater than 0.2, preferably greater than 0.3, particularly preferably greater than 1 and/or is in the range from 0.2 to 50, preferably in the range from 0.3 to 20, particularly preferably in the range from 1 to 10.

Preference is given to a process according to the invention (preferably as described above as preferred), wherein the ratio of the combined total weight of all of the compounds (A) and all of the compounds (S) to the total weight of all of the radically polymerizable organic monomers (M) lies in the range from 0.05 to 10% by weight, preferably in the range from 0.5 to 7% by weight and/or wherein the total content of radically polymerizable organic monomers (M) lies in the range from 15 to 95% by weight, preferably in the range from 25 to 40% by weight, based on the total weight of the composition and/or wherein the combined total content of all of the compounds (A) and all of the compounds (S) lies in the range from 0.05 to 7% by weight, preferably in the range from 0.1 to 2.5% by weight, based on the total weight of the composition.

Particular preference is given, under consideration of the preceding remarks, to a process according to the invention (preferably as described above as preferred), wherein the one or at least one of the several radically polymerizable organic monomers (M)

is selected from the group consisting of monomers with at least two ethylenic groups (M1), wherein the monomers with at least two ethylenic groups (M1) are selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, glycerol 1,3-dimethacrylate, tetraethylene glycol dimethacrylate, neopentyl glycol dimethacrylate, 2,2-bis[4-[3-methacryloyloxy-2-hydroxypropoxy]phenyl]propane and the di(meth)acrylates of dihydroxymethyltricyclo[5.2.1.0$^{2,6}$]decane and/or wherein the one or at least one of the several or at least one additional of the several radically polymerizable organic monomers (M)

is selected from the group consisting of hydroxyl compounds with at least one ethylenic group (M2), wherein the hydroxyl compounds with at least one ethylenic group (M2) are selected from the group consisting of 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate and 2,2-bis[4-[3-methacryloyloxy-2-hydroxypropoxy]phenyl]propane and/or wherein the one or at least one of the several compounds (A) is selected from the group consisting of ascorbic acid, sodium ascorbate, isoascorbic acid and sodium isoascorbate and/or wherein the one or at least one of the several compounds (S) is selected from the group consisting of toluenesulfinic acid, sodium toluenesulfinate, potassium toluenesulfinate, benzenesulfinic acid, sodium benzenesulfinate and potassium benzenesulfinate and/or wherein the ratio of the total molar amount of all of the compounds (A) to the total molar amount of all of the compounds (S)

is greater than 1 and/or lies in the range from 1 to 10 and/or wherein the ratio of the combined total weight of all of the compounds (A) and all of the compounds (S) to the total weight of all of the radically polymerizable organic monomers (M) lies in the range from 0.5 to 7% by weight and/or wherein the total content of radically polymerizable organic monomers (M) lies in the range from 25 to 40% by weight, based on the total weight of the composition
and/or
wherein the combined total content of all of the compounds (A) and all of the compounds (S) lies in the range from 0.1 to 2.5% by weight, based on the total weight of the composition.

Preferably, within this context, the "and" is valid for each "and/or" linkage.

Preference is given to a process according to the invention (preferably as described above as preferred), additionally comprising the stage:
stage (e) production or provision of a basic glass composition (G) as crosslinking agent for polymers containing carboxylic acid groups (P) selected from the group consisting of homo- and copolymers of an α,β-unsaturated carboxylic acid (C),
wherein stage (d) comprises the mixing of the monomers (M) with the compounds (A) and (S) and also with the glass composition (G) produced or provided in stage (e).

Stage (e) is preferably carried out before the beginning of stage (d). Stage (d) can comprise substages.

This process according to the invention is preferred since compositions according to the invention can be manufactured as component of a multicomponent resin-modified glass ionomer cement which already comprise a basic glass composition (G) and accordingly can be effectively used in two-component resin-modified glass ionomer cements.

Preference is given to a process according to the invention (preferably as described to above as preferred), wherein the basic glass composition (G) comprises one or more cations of elements which are selected from the group consisting of the metals of Main Groups I, II and III of the Periodic Table, are preferably selected from the group consisting of sodium, potassium, calcium and aluminum,
and which are particularly preferably present in the form of one or more compounds selected from the group consisting of oxides, hydroxides, sulfates, nitrates, phosphates, carbonates, silicates, fluorides and nitrides
and/or
wherein the basic glass composition (G) comprises an aluminum fluorosilicate glass
and/or
wherein the basic glass composition (G) comprises one or more glasses with organically modified surface, preferably with silanized surface.

Corresponding processes are likewise advantageous because preferred compositions are obtained with them.

Preference is given to a process according to the invention (preferably as described above as preferred), additionally comprising the stage:
stage (f) synthesis or provision of one or more additional constituents (B) selected from the group consisting of photoinitiators, inhibitors, compounds (Z) and additives,
wherein stage (d) comprises the mixing of the monomers (M) with the compounds (A) and (S) and also with the one or the several additional constituents (B).

Within this context
the photoinitiators are preferably selected from the group consisting of benzoin alkyl ethers, benzoin alkyl esters, benzil monoketals, acylphosphine oxides, benzophenones, acetophenones, ketals, thioxanthones, titanocenes, aliphatic 1,2-diketo compounds and aromatic 1,2-diketo compounds, are preferably selected from the group comprising 2,2-diethoxyacetophenone, 9,10-phenanthrenequinone, diacetyl, furil, anisil, 4,4'-dichlorobenzil and 4,4'-dialkoxybenzil and camphorquinone,
the inhibitors are preferably selected from the group consisting of substituted phenols, phenothiazine, stable organic radicals and hydroquinone monomethyl ether, are particularly preferably selected from the group consisting of 2,6-di(tert-butyl)-4-methylphenol, hydroquinone monomethyl ether, the 2,2-diphenyl-1-picrylhydrazyl radical, the galvinoxyl radical, the triphenylmethyl radical and the 2,2,6,6-tetramethylpiperidinyl-1-oxyl radical,
the compounds (Z) are selected from the group consisting of barbituric acids, tertiary amines and secondary amines
and
the additives are selected from the group consisting of colorants, tartaric acid, silica, stabilizers, modifiers, bactericidal substances and inert fillers. (Preferred additives are defined above associated with compositions according to the invention.)

This process according to the invention is preferred because preferred compositions according to the invention are accordingly obtained. Stage (f) is preferably carried out before the beginning of stage (d). Stage (d) can comprise substages.

Preference is given to a process according to the invention for the preparation of a cured dental material (preferably as described above as preferred), additionally comprising the stage:
stage (g) curing of a mixture comprising the composition prepared, wherein the curing preferably comprises:
the reaction of the compounds (A) and (S) present in the mixture with one or more oxidizing agents (O) selected from the group consisting of persulfates, permanganates, perborates, peroxides and hydroperoxides
and/or
the irradiation of the mixture with light having a wavelength in the range from 300 to 700 nm, preferably in the range from 350 to 600 nm
and/or
the reaction of polymers containing carboxylic acid groups (P) selected from the group consisting of homo- and copolymers of an α,β-unsaturated carboxylic acid (C) present in the mixture with a basic glass composition (G) present in the mixture as crosslinking agent for polymers containing carboxylic acid groups (P) selected from the group consisting of homo- and copolymers of an α,β-unsaturated carboxylic acid (C), wherein the α,β-unsaturated carboxylic acid (C) is preferably selected from the group consisting of acrylic acid, methacrylic acid, itaconic acid, fumaric acid, maleic acid, chloromethacrylic acid, cyanomethacrylic acid, aconitic acid, mesaconic acid, glutaconic acid and citraconic acid, is preferably selected from the group consisting of acrylic acid and maleic acid, and/or wherein the weight-average molecular weight $M_w$ of the total amount of the polymers containing carboxylic acid groups (P) preferably lies in the range from 1000 to 150 000 g/mol, preferably between 40 000 and 100 000 g/mol.

"Curing" means that at least some of the constituents of the mixture comprising the composition manufactured are polymerized. The curing begins with the initiation of the polymerization. A complete consumption by reaction of all of the polymerizable constituents of the composition is not necessary and is in practice regularly not achieved. For preferred multicomponent resin-modified glass ionomer cements according to the invention, it is necessary for the curing already to begin immediately after the mixing of the components and with the beginning of the polymerization of the monomers (M) or the beginning of the GIC setting.

The composition according to the invention manufactured in a process according to the invention is preferably mixed with additional constituents, in order to manufacture a mixture. This mixture is cured according to the invention in stage (g). A corresponding mixture is, for example, obtained if the first component of a multicomponent resin-modified glass ionomer cement according to the invention which comprises the composition according to the invention is mixed with an individual or several additional components of the multicomponent resin-modified glass ionomer cement according to the invention.

For example, the mixing of the components for the case of a two-component resin-modified glass ionomer cement according to the invention in the paste/paste form can be carried out mechanically and automatically using an appropriate cartridge system with static mixer for direct application. In the direct application, appropriately sized two-chambered cartridges are first filled with the components. The preparation of a mixture comprising the composition according to the invention in application is then carried out by expressing the pastes from the two-chambered cartridge using a dual plunger through a static mixing needle on the tooth to be treated in the inside of the mouth. A different pigmentation of the two unmixed components makes it possible, after the pastes have passed through the mixing needle, from the resulting shade, to examine the homogeneity of the mixing.

The application of a composition according to the invention to give a mixture comprising the composition according to the invention can also, of course, be carried out by mixing by hand. For the case of a two-component resin-modified glass ionomer cement according to the invention in the paste/liquid form, generally a successive mixing process is carried out, in which a predetermined amount of the paste is mixed together stepwise with a predetermined amount of the liquid using a mixing device. This procedure can also be used analogously in the case of the paste/paste form.

For the case of a two-component resin-modified glass ionomer cement according to the invention, the mixing ratio of the two components can be between 10:1 and 1:10 and preferably lies between 1:4 and 4:1 and very particularly preferably is 1:1, based on the weight used of the two components.

The mixture comprising the composition according to the invention prepared has to be cured. This is preferably carried out in at least one, preferably at least two, of three ways explained below:

If the curing is initiated through the reaction of the compounds (A) and (S) present in the mixture with one or more oxidizing agents (O) selected from the group consisting of persulfates, permanganates, perborates, peroxides and hydroperoxides, this is a chemical curing by means of a redox polymerization initiator system. Such a curing is also described as self-curing.

If the curing is initiated through the irradiation of the mixture with light having a wavelength in the range from 300 to 700 nm, preferably in the range from 350 to 600 nm, a person skilled in the art speaks of a light-induced curing. This curing presupposes the presence of at least one photoinitiator in the mixture comprising the composition according to the invention prepared.

If the curing is carried out by the reaction of polymers containing carboxylic acid groups (P) selected from the group consisting of homo- and copolymers of an α,β-unsaturated carboxylic acid (C) present in the mixture with a basic glass composition (G) present in the mixture as crosslinking agent for polymers containing carboxylic acid groups (P) selected from the group consisting of homo- and copolymers of an α,β-unsaturated carboxylic acid (C), a person skilled in the art speaks of a GIC setting.

The curing of the mixture comprising the composition prepared is preferably carried out by at least two of the three abovementioned curing mechanisms, the GIC setting (as defined above) representing one of these at least two curing mechanisms, and very particularly preferably according to all of the three abovementioned curing mechanisms.

Preference is therefore particularly given to a process according to the invention for the preparation of a cured dental material (preferably as described above as preferred), additionally comprising the stage:

stage (g) curing of a mixture comprising the composition manufactured, wherein the curing preferably comprises:

the reaction of the compounds (A) and (S) present in the mixture with one or more oxidizing agents (O) selected from the group consisting of persulfates, permanganates, perborates, peroxides and hydroperoxides and the irradiation of the mixture with light having a wavelength in the range from 300 to 700 nm, preferably in the range from 350 to 600 nm and the reaction of polymers containing carboxylic acid groups (P) selected from the group consisting of homo- and copolymers of an α,β-unsaturated carboxylic acid (C) present in the mixture with a basic glass composition (G) present in the mixture as crosslinking agent for polymers containing carboxylic acid groups (P) selected from the group consisting of homo- and copolymers of an α,β-unsaturated carboxylic acid (C), wherein the α,β-unsaturated carboxylic acid (C) is preferably selected from the group consisting of acrylic acid, methacrylic acid, itaconic acid, fumaric acid, maleic acid, chloromethacrylic acid, cyanomethacrylic acid, aconitic acid, mesaconic acid, glutaconic acid and citraconic acid, is preferably selected from the group consisting of acrylic acid and maleic acid and/or wherein the weight-average molecular weight $M_w$ of the total amount of the polymers containing carboxylic acid groups (P) preferably lies in the range from 1000 to 150 000 g/mol, preferably between 40 000 and 100 000 g/mol.

Such preferred processes according to the invention in practice regularly show superior setting kinetics for the mixture prepared and still allow, even after storage for several weeks of the components necessary for the preparation of the mixture, a reliable and fast curing. The curing with three different curing mechanisms makes the process particularly insusceptible to malfunctions which affect simply one of the curing mechanisms, such as, for example, a decomposition of the photoinitiator. The mixtures comprising the composition prepared, for example a resin-modified glass ionomer cement according to the invention, whose originally separate components are already mixed, can be directly applied on the tooth in the mouth of the patient or can also be used outside the mouth, for example on a prosthesis, the prosthesis being subsequently cemented in the mouth.

The present invention also relates to the use of a composition according to the invention (as defined above, preferably as described above as preferred) as component of a multicomponent resin-modified glass ionomer cement, preferably of a multicomponent resin-modified glass ionomer cement according to the invention.

In addition, the present invention relates to the use of one or more compounds (S) selected from the group consisting of sulfinic acids, salts of sulfinic acids and salts of organoboron compounds or of mixtures comprising one or more compounds (S) selected from the group consisting of sulfinic acids, salts of sulfinic acids and salts of organoboron compounds, for (i) increasing the storage stability of a composition comprising one or more compounds (A) selected from the group consisting of the isomers of ascorbic acid, the salts of the isomers of ascorbic acid, the esters of the isomers of ascorbic acid and the ethers of the isomers of ascorbic acid (as defined above within the context of other aspects of the invention, preferably as described above as preferred)

and one or more radically polymerizable organic monomers (M) (as defined above in connection with other aspects of the invention, preferably as described above as preferred)

and/or (ii) manufacturing a composition according to the invention (as defined above, preferably as described above as preferred).

Surprisingly, it has been shown that the storage stability of a composition comprising one or more compounds (A) and one or more radically polymerizable organic monomers (M) can be increased if one or more compounds (S) or a mixture comprising one or more compounds (S) are added to the composition. Within this context, it is particularly surprising that the negative effects of the compounds (A) functioning as reducing agents can be reduced by adding one or more compounds (S) to the composition, although these themselves can regularly act as reducing agents.

The use according to the invention also relates to the manufacturing of compositions according to the invention (as defined above, preferably as described above as preferred).

Particular preference is given to the use according to the invention of one or more corns pounds (S) selected from the group consisting of sulfinic acids, salts of sulfinic acids and salts of organoboron compounds or of mixtures comprising one or more compounds (S) selected from the group consisting of sulfinic acids, salts of sulfinic acids and salts of organoboron compounds, for (i) increasing the storage stability of a composition comprising one or more compounds (A) selected from the group consisting of the isomers of ascorbic acid, the salts of the isomers of ascorbic acid, the esters of the isomers of ascorbic acid and the ethers of the isomers of ascorbic acid and one or more radically polymerizable organic monomers (M)

and (ii) manufacturing a composition according to the invention.

Preference is given to a use according to the invention (preferably as described above as preferred), wherein the one or at least one of the several compounds (S) is selected from the group consisting of aromatic sulfinic acids, salts of aromatic sulfinic acids and salts of aromatic organoboron compounds, is preferably selected from the group consisting of toluenesulfinic acid, sodium toluenesulfinate, potassium toluenesulfinate, benzenesulfinic acid, sodium benzenesulfinate, potassium benzenesulfinate, sodium tetraphenylborate and lithium tetraphenylborate, is particularly preferably selected from the group consisting of toluenesulfinic acid, sodium toluenesulfinate, potassium toluenesulfinate, benzenesulfinic acid, sodium benzenesulfinate and potassium benzenesulfinate and/or wherein the one or at least one of the several compounds (A) is selected from the group consisting of ascorbic acid, salts of ascorbic acid, isoascorbic acid and salts of isoascorbic acid, is preferably selected from the group consisting of ascorbic acid, sodium ascorbate, isoascorbic acid and sodium isoascorbate and/or wherein the one or at least one of the several radically polymerizable organic monomers (M)

is selected from the group consisting of monomers with at least two ethylenic groups (M1), wherein the monomers with at least two ethylenic groups (M1) are preferably selected from the group consisting of diacrylates, triacrylates, dimethacrylates, trimethacrylates, are particularly preferably selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, glycerol 1,3-dimethacrylate, tetraethylene glycol dimethacrylate, neopentyl glycol dimethacrylate, 2,2-bis[4-[3-methacryloyloxy-2-hydroxypropoxy]phenyl]propane and the di(meth)acrylates of dihydroxymethyltricyclo[5.2.1.0$^{2,6}$]decane and/or wherein the one or at least one of the several or at least one additional of the several radically polymerizable organic monomers (M)

is selected from the group consisting of hydroxyl compounds with at least one ethylenic group (M2), wherein the hydroxyl compounds with at least one ethylenic group (M2) are preferably selected from the group consisting of 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate and 2,2-bis[4-[3-methacryloyloxy-2-hydroxypropoxy]phenyl]propane.

As explained above within the context of the correspondingly preferred compositions according to the invention, the surprising technical effect of the present invention is shown especially pronounced with use of the compounds defined above and very especially pronounced with use of the compounds described above as preferred. In separate tests, it has in particular been shown that the use according to the invention is particularly advantageous if several of the compounds disclosed as preferred are combined.

Particular preference is accordingly given, for example, to a use according to the invention (preferably as described above as preferred),
wherein the one or at least one of the several compounds (S) is selected from the group consisting of toluenesulfinic acid, sodium toluenesulfinate, potassium toluenesulfinate, benzenesulfinic acid, sodium benzenesulfinate and potassium benzenesulfinate
and
wherein the one or at least one of the several compounds (A) is selected from the group consisting of ascorbic acid, sodium ascorbate, isoascorbic acid and sodium isoascorbate.

This combination of compounds (S) and (A) is generally particularly preferred within the framework of the present invention.

In the use according to invention, the surprising effect is shown particularly clearly for the ratios of weights and molar amounts which have already been disclosed above as preferred within the context of compositions according to the invention. Preference is accordingly given to a use according to the invention (preferably as described above as preferred),
wherein the ratio of the total molar amount of all of the compounds (A) to the total molar amount of all of the compounds (S)
is greater than 0.2, preferably greater than 0.3, particularly preferably greater than 1
and/or
is in the range from 0.2 to 50, preferably in the range from 0.3 to 20, particularly preferably in the range from 1 to 10
and/or
wherein the ratio of the combined total weight of all of the compounds (A) and all of the compounds (S) to the total weight of all of the radically polymerizable organic monomers (M) lies in the range from 0.05 to 10% by weight, preferably in the range from 0.5 to 7% by weight
and/or
wherein the total content of radically polymerizable organic monomers (M) lies in the range from 15 to 95% by weight, preferably in the range from 25 to 40% by weight, based on the total weight of the composition
and/or
wherein the combined total content of all of the compounds (A) and all of the compounds (S) lies in the range from 0.05 to 7% by weight, preferably in the range from 0.1 to 2.5% by weight, based on the total weight of the composition.

Closely connected to the existing inventive use is a process for increasing the storage stability of a composition comprising
one or more compounds (A) selected from the group consisting of the isomers of ascorbic acid, the salts of the isomers of ascorbic acid, the esters of the isomers of ascorbic acid and the ethers of the isomers of ascorbic acid, and
one or more radically polymerizable organic monomers (M) (as defined above within the context of other aspects of the invention, preferably as described above as preferred),
with the following stage:
mixing the composition with one or more compounds (S) selected from the group consisting of sulfinic acids, salts of sulfinic acids and salts of organoboron compounds (as defined above also within the context of other aspects of the invention, preferably as described above as preferred).

The corresponding process, as also the use according to the invention, is particularly advantageous because (base) compositions, the storage stability of which is insufficient, can be so modified thereby that a composition with improved storage stability is obtained.

Particular preference is given, in the process disclosed above, to the one or at least one of the compounds (S) and/or the one or at least one of the compounds (A) and/or the one or at least one of the radically polymerizable organic monomers (M) defined as is defined above for preferred compositions according to the invention, preferred kits according to the invention, preferred processes according to the invention or preferred uses according to the invention.

The invention also relates to a cured dental material comprising
one or more oxidation products of one or more compounds (A) selected from the group consisting of the isomers of ascorbic acid, the salts of the isomers of ascorbic acid, the esters of the isomers of ascorbic acid and the ethers of the isomers of ascorbic acid (as defined above within the context of other aspects of the invention, preferably as described above as preferred),
one or more oxidation products of one or more compounds (S) selected from the group consisting of sulfinic acids, salts of sulfinic acids and salts of organoboron compounds (as defined above within the context of other aspects of the invention, preferably as described above as preferred)
and
a polymer comprising units of (co)polymerized radically polymerizable organic monomers (M) (as defined above within the context of other aspects of the invention, preferably as described above as preferred).

A cured dental material, i.e. a dental material in which the curing has already at least partially started, which is prepared using a composition according to the invention, from a kit according to the invention or with the help of a process according to the invention, has the characteristics described above, so that its preparation history can be understood. It is particularly advantageous within this context for the oxidation products of the compounds (A) and (S), i.e. the chemical compounds into which the compounds (A) and (S) are each converted, if they react as reducing agents in a redox polymerization initiator system and accordingly are themselves oxidized, to have no negative effects on the mechanical properties and/or the compatibility and/or the aging behavior of the cured dental materials.

It follows, from the preferred embodiments of the compositions according to the invention, of the kits according to the invention, of the process according to the invention and of the use according to the invention, that cured dental materials according to the above definition are preferred, wherein the one or at least one of the several compounds (S) is selected from the group consisting of aromatic sulfinic acids, salts of aromatic sulfinic acids and salts of aromatic organoboron compounds, is preferably selected from the group consisting of toluenesulfinic acid, sodium toluenesulfinate, potassium toluenesulfinate, benzenesulfinic acid, sodium benzenesulfinate, potassium benzenesulfinate, sodium tetraphenylborate and lithium tetraphenylborate, is particularly preferably selected from the group consisting of toluenesulfinic acid, sodium toluenesulfinate, potassium toluenesulfinate, benzenesulfinic acid, sodium benzenesulfinate and potassium benzenesulfinate and/or wherein the one or at least one of the several compounds (A) is selected from the group consisting of ascorbic acid, salts of ascorbic acid, isoascorbic acid and salts of isoascorbic acid, is preferably selected from the group consisting of ascorbic acid, sodium ascorbate, isoascorbic acid and sodium isoascorbate and/or wherein the one or at least one of the several radically polymerizable organic monomers (M)

is selected from the group consisting of monomers with at least two ethylenic groups (M1), wherein the monomers with at least two ethylenic groups (M1) are preferably selected from the group consisting of diacrylates, triacrylates, dimethacrylates, trimethacrylates, are particularly preferably selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, glycerol 1,3-dimethacrylate, tetraethylene glycol dimethacrylate, neopentyl glycol dimethacrylate, 2,2-bis[4-[3-methacryloyloxy-2-hydroxypropoxy]phenyl]propane and the di(meth)acrylates of dihydroxymethyltricyclo[5.2.1.0$^{2,6}$]decane and/or wherein the one or at least one of the several or at least one additional of the several radically polymerizable organic monomers (M)

is selected from the group consisting of hydroxyl compounds with at least one ethylenic group (M2), wherein the hydroxyl compounds with at least one ethylenic group (M2) are preferably selected from the group consisting of 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate and 2,2-bis[4-[3-methacryloyloxy-2-hydroxypropoxy]phenyl]propane.

It furthermore follows, from the preferred embodiments of the compositions according to the invention, of the kits according to the invention, of the process according to the invention and of the use according to the invention, that cured dental materials (preferably as described above as preferred) are preferred, which additionally comprise the product of the crosslinking of one or more polymers containing carboxylic acid groups (P) selected from the group consisting of homo- and copolymers of an α,β-unsaturated carboxylic acid (C) with a basic glass composition (G), wherein the α,β-unsaturated carboxylic acid (C) is preferably selected from the group consisting of acrylic acid, methacrylic acid, itaconic acid, fumaric acid, maleic acid, chloromethacrylic acid, cyanomethacrylic acid, aconitic acid, mesaconic acid, glutaconic acid and citraconic acid, is preferably selected from the group consisting of acrylic acid and maleic acid, wherein the weight-average molecular weight $M_w$ of the total amount of the polymers containing carboxylic acid groups (P) lies in the range from 1000 to 150 000 g/mol, preferably between 40 000 and 100 000 g/mol, wherein the basic glass composition (G) preferably comprises one or more cations of elements which are selected from the group consisting of the metals of Main Groups I, II and III of the Periodic Table, are preferably selected from the group consisting of sodium, potassium, calcium and aluminum, and which are particularly preferably present in the form of one or more compounds selected from the group consisting of oxides, hydroxides, sulfates, nitrates, phosphates, carbonates, silicates, fluorides and nitrides and/or comprises an aluminum fluorosilicate glass and/or comprises one or more glasses with organically modified surface, preferably with silanized surface.

The preferred embodiments defined above within the context of other aspects of the invention are in this respect correspondingly preferred, mutatis mutandis.

Preference is given to a cured dental material defined above (preferably as described above as preferred) which can be prepared according to a process according to the invention.

The invention is described in more detail below on the basis of examples, the examples relating to those compositions according to the invention or two-component resin-modified glass ionomer cements according to the invention which are optimized for use as luting cements. However, a person skilled in the art knows how he modifies a basic dental composition for the different dental applications. The mechanical properties of dental compositions have to be different depending on the indications. Thus, a luting cement does not need low abrasion values. Conversely, a filling material does not need a low film thickness. Both systems, however, need a good adhesion. A person skilled in the art is in a position to adjust these properties. Thus, for a filling material, he would select a higher filler content with a completely different particle size distribution in comparison to a luting cement.

EXAMPLES

Preparation of the Starting Components:

Two separate components in the form of pastes were first prepared as starting point for the experiments carried out. These components are subsequently described as Paste A and Paste B. The compositions of Paste A and of Paste B can each be taken from the following Table 1.

TABLE 1

Compositions of Paste A and of Paste B (contents are each given in parts by weight and are based on the respective paste).

| Paste A | | Paste B | |
|---|---|---|---|
| Constituent | Amount | Constituent | Amount |
| PAA | 19.00 | HEMA | 19.00 |
| Water | 19.00 | GDMA | 7.50 |
| HEMA | 18.00 | TEGDMA | 0.80 |
| GDMA | 3.30 | UDMA | 3.20 |

TABLE 1-continued

Compositions of Paste A and of Paste B (contents are each given in parts by weight and are based on the respective paste).

| Paste A | | Paste B | |
|---|---|---|---|
| Constituent | Amount | Constituent | Amount |
| BHT | 0.05 | CQ | 0.08 |
| Aerosil | 2.50 | DABE | 0.11 |
| TMHP | 0.15 | BHT | 0.05 |
| Inert glass | 38.00 | Aerosil | 3.50 |
| | | AFS | 65.76 |

The abbreviations used in Table 1 are assigned in Table 2 to the corresponding chemical compounds.

TABLE 2

Abbreviations used.

| Abbreviation | Compound | Function |
|---|---|---|
| PAA | Polyacrylic acid | Polymer containing carboxylic acid groups (P) |
| Water | H₂O (demineralized) | |
| HEMA | 2-Hydroxyethyl methacrylate | Monomer (M) |
| GDMA | Glycerol 1,3-dimethacrylate | Monomer (M) |
| TEGDMA | Triethylene glycol dimethacrylate | Monomer (M) |
| UDMA | Urethane dimethacrylate | Monomer (M) |
| Aerosil | Pyrogenic silica | Inert filler |
| AFS | Aluminum fluorosilicate glass | Basic glass composition (G) |
| BHT | 2,6-Di(tert-butyl)hydroxytoluene | Inhibitor |
| CQ | DL-Camphorquinone | Photoinitiator |
| DABE | 4-Dimethylaminobenzoic acid ethyl ester | Reducing agent; Compound (Z) |
| TMHP | 1,1,3,3-Tetramethylbutyl hydroperoxide | Oxidizing agent (O) |

For the preparation of the Pastes A and B, the constituents were each weighed out, homogenized on a mixer (SpeedMixer™ DAC 600.1 VAC-P, Hauschild & Co KG, Hamm, Germany), rolled on a three roll mill (Exakt, Norderstedt, Germany) and subsequently deaerated on a vacuum mixer (SpeedMixer™ DAC 600.1 VAC-P) at −0.9 bar vacuum.

Preparation of the Samples:

Starting from Paste B, compositions according to the claims in the form of pastes (e.g. B-I2), i.e. compositions for use as component of a multicomponent resin-modified glass ionomer cement, and also comparative compositions (e.g. B-C1) which are based on the state of the art, were prepared by mixing with additional constituents. For this, each time a certain amount of the Paste B prepared was mixed with one or more additional substances. The chemical compositions of the compositions prepared in this way (modified Paste B) are recorded in Tables 3 and 4.

The abbreviations used in Tables 3 and 4 are assigned in Table 5 to the corresponding chemical compounds.

TABLE 3

Composition of the compositions prepared starting from Paste B (modified Paste B; according to the invention; contents are each given in parts by weight and are based on the respective composition).

| Constituent | B-I1 | B-I2 | B-I3 | B-I4 | B-I5 | B-I6 |
|---|---|---|---|---|---|---|
| Paste B | 99.47 | 99.47 | 99.47 | 99.47 | 99.41 | 99.23 |
| AA | 0.50 | 0.48 | 0.26 | 0.13 | | 0.26 |
| NaIA | | | | | 0.32 | |
| NaTS | 0.03 | 0.05 | 0.27 | 0.40 | 0.27 | |
| NaTPB | | | | | | 0.51 |

TABLE 4

Composition of the compositions prepared (modified Paste B; comparative; contents are each given in parts by weight and are based on the respective composition).

| Constituent | B-C1 | B-C2 | B-C3 | B-C4 | B-C5 | B-C6 | B-C7 |
|---|---|---|---|---|---|---|---|
| Paste B | 99.47 | 99.46 | 99.55 | 99.54 | 99.47 | 99.46 | 99.45 |
| AA | 0.53 | | 0.26 | | 0.48 | | |
| NaTS | | 0.54 | | 0.27 | | 0.49 | 0.45 |
| OA | | | 0.19 | 0.19 | | | |
| NaDS | | | | | 0.05 | | |
| Fe(II) | | | | | | 0.05 | 0.10 |

TABLE 5

Abbreviations used.

| Abbreviation | Compound |
|---|---|
| AA | Ascorbic acid |
| NaIA | Sodium isoascorbate |
| NaTS | Sodium p-toluenesulfinate |
| NaTPB | Sodium tetraphenylborate |
| NaDS | Sodium disulfite |
| Fe(II) | Iron(II) chloride tetrahydrate |
| OA | Oxalic acid |

For the preparation of the compositions, the constituents were each weighed out, homogenized on a mixer (SpeedMixer™ DAC 600.1 VAC-P, Hauschild & Co KG, Hamm, Germany), rolled on a three roll mill (Exakt, Norderstedt, Germany) and subsequently deaerated on a vacuum mixer (SpeedMixer™ DAC 600.1 VAC-P) at −0.9 bar vacuum.

In the compositions which, in addition to Paste B, comprise even more than one additional constituent, the molar amount ratios of the additional constituents are combined in Table 6.

TABLE 6

Molar amount ratio of the constituents added to the Paste B in the sample preparation.

| Sample | Constituent 1 | Molar amount ratio | Constituent 2 |
|---|---|---|---|
| B-I1 | AA | 20:1 | NaTS |
| B-I2 | AA | 10:1 | NaTS |
| B-I3 | AA | 1:1 | NaTS |
| B-I4 | AA | 1:3 | NaTS |
| B-I5 | NaIA | 1:1 | NaTS |

TABLE 6-continued

Molar amount ratio of the constituents added to the Paste B in the sample preparation.

| Sample | Constituent 1 | Molar amount ratio | Constituent 2 |
|---|---|---|---|
| B-I6 | AA | 1:1 | NaTPB |
| B-C3 | AA | 1:1 | OA |
| B-C4 | NaTS | 1:1 | OA |
| B-C5 | AA | 10:1 | NaDS |
| B-C6 | NaTS | 10:1 | Fe(II) |
| B-C7 | NaTS | 5:1 | Fe(II) |

Each of the compositions prepared (according to the invention and comparative examples) is a composition for use as component of a multicomponent resin-modified glass ionomer cement.

Each of the compositions prepared (according to the invention and comparative exams pies) is each time a component of a two-component resin-modified glass ionomer cement and forms each time a two-component resin-modified glass ionomer cement with the same amount of Paste A. This means that, for example, the composition according to the invention B-I2 forms a two-component resin-modified glass ionomer cement with Paste A, just as the comparative composition B-C5 forms a two-component resin-modified glass ionomer cement with Paste A.

Experimental Procedure:

Two-chambered syringes (5 ml, 1:1, SDL X05-01-52, PED X05-01-SI, Sulzer Mixpac AG, Haag, Switzerland) were filled with the two-component resin-modified glass ionomer cements prepared (modified Paste B; Paste A). After filling, the two-chambered syringes were stored at a temperature of 37° C.

After defined intervals (initial, that is directly after filling, and also after 1, 2, 4, 6, 8, 10 and 12 weeks), the syringes were withdrawn and, after each time bringing to ambient temperature—as far as possible—the setting time and the bending strength of the cured resin-modified glass ionomer cement prepared by mixing the components were determined (the determination methods are given further below). For the mixing, the appropriate static mixers (ML 2.5-16-S, Sulzer Mixpac AG) were put on the syringes and—as far as possible—the two respective components of the two-component resin-modified glass ionomer cements were expressed with a plunger (PLH X05-01-46) and mixed homogeneously in the ratio 1:1.

The storage stability of a composition is primarily dependent on whether it is or is not stable without mixing with an additional component each time over a certain period of time without significant polymerization, i.e. chemically virtually unchanged. A composition (in particular paste) which, under the abovementioned storage conditions, is still not cured (polymerized) even after twelve weeks, is more stable on storage than a composition (paste) which, after e.g. six weeks, is already so cured (polymerized) that mixing with the assigned additional component is no longer possible.

Provided that a composition can be mixed at a certain instant with an assigned additional component and that the resulting glass ionomer cement can be cured, the curing time and the flexural strength of the cured glass ionomer cement are further indicators for the storage stability of the composition (paste) tested.

Determination of the Setting Time:

For the determination of the setting time, the material to be tested was cured exclusively chemically. The setting time was determined on a rheometer (Physica MCR 301, Anton Paar GmbH, Graz, Austria) For this, the viscosity as a function of the time was recorded at 37° C. in an oscillation measurement (deflection/amplitude=1%, f=4 Hz). The resin-modified glass ionomer cement was mixed as described above and applied to the measuring plate of a plate/plate system (D=12 mm, gap=1 mm). The time was started with the beginning of the mixing. The time from the beginning of mixing until a viscosity of $10^4$ Pa·s was achieved was defined as setting time.

Determination of the Flexural Strength:

For the determination of the flexural strength, the material to be tested was cured exclusively chemically. The flexural strength was determined according to ISO 9917-2:2010. The glass ionomer cement was mixed as described above and each time corresponding Teflon molds were filled with it, without the presence of air bubbles, the cement being covered with a film and a glass plate. The excess was squeezed out using a screw clamp. The test specimens were cured at 37° C. for 24 hours in a water bath. The dimensions of the test specimen (2 mm×2 mm) were measured in the middle with a measurement accuracy of 0.01 mm. Subsequently, the test specimens were loaded with a universal test apparatus (Zwick GmbH, Ulm, Germany) with a feed rate of 0.75 mm/min until breaking occurred.

Results:

The results of the experiments are combined in the following table 7 (flexural strength) and table 8 (setting time).

TABLE 7

| Storage duration | Flexural strength results |||||||||||||
|---|---|---|---|---|---|---|---|---|---|---|---|---|
| | Flexural strength/MPa |||||||||||||
| | B-I1 | B-I2 | B-I3 | B-I4 | B-I5 | B-I6 | B-C1 | B-C2 | B-C3 | B-C4 | B-C5 | B-C6 | B-C7 |
| Initial | 24.7 | 23.6 | 22.3 | 25.5 | 25.2 | 26.8 | 24.9 | Y | P | Y | 20.2 | P | P |
| 1st Week | 27.7 | 26.3 | 26.2 | 23.0 | 24.9 | 23.7 | 22.7 | — | — | — | 21.4 | — | — |
| 2nd Week | 25.9 | 27.1 | 26.7 | 18.6 | 23.9 | 27.3 | 25.9 | — | — | — | 24.8 | — | — |
| 4th Week | 28.3 | 27.2 | 18.3 | 27.0 | 24.9 | 26.9 | 23.6 | — | — | — | 21.9 | — | — |
| 6th Week | 27.5 | 22.1 | 18.9 | 19.0 | 25.1 | 23.7 | P | — | — | — | P | — | — |
| 8th Week | 27.1 | 28.7 | 14.9 | 18.3 | 26.8 | 25.1 | — | — | — | — | — | — | — |
| 10th Week | 21.9 | 23.5 | 9.6 | 12.0 | 25.2 | 23.9 | — | — | — | — | — | — | — |
| 12th Week | 8.1 | 27.0 | 7.3 | X | 18.9 | 22.3 | — | — | — | — | — | — | — |

TABLE 8

Setting time results.

| Storage duration | Setting time/s | | | | | | | | | | | | |
|---|---|---|---|---|---|---|---|---|---|---|---|---|---|
| | B-I1 | B-I2 | B-I3 | B-I4 | B-I5 | B-I6 | B-C1 | B-C2 | B-C3 | B-C4 | B-C5 | B-C6 | B-C7 |
| Initial | 113 | 110 | 120 | 153 | 135 | 73 | 120 | Y | P | Y | 72 | P | P |
| 1st Week | 107 | 130 | 135 | 175 | 145 | 110 | 114 | — | — | — | 50 | — | — |
| 2nd Week | 104 | 129 | 153 | 162 | 148 | 125 | 117 | — | — | — | 61 | — | — |
| 4th Week | 116 | 120 | 187 | 196 | 160 | 132 | 90 | — | — | — | 101 | — | — |
| 6th Week | 107 | 123 | 213 | 189 | 154 | 145 | P | — | — | — | P | — | — |
| 8th Week | 115 | 116 | 234 | 243 | 146 | 164 | — | — | — | — | — | — | — |
| 10th Week | 211 | 135 | 259 | 298 | 166 | 162 | — | — | — | — | — | — | — |
| 12th Week | 281 | 170 | 267 | 326 | 175 | 168 | — | — | — | — | — | — | — |

In tables 7 and 8, particular experimental results are identified with the letters "X", "Y" or The entry "X" means that the corresponding two-component resin-modified glass ionomer cement admittedly after the mixing still reached a viscosity of $10^4$ Pa·s, so that a setting time could be determined, but no sufficiently solid test specimen for the determination of the flexural strength could be obtained.

The entry "P" means that the corresponding composition is polymerized, i.e. cured, during storage. This means that the corresponding composition could no longer be expressed from the two-chambered syringe and accordingly could not be mixed with Paste A under the experimental conditions chosen. The entry "P" accordingly characterizes the complete loss of the storage stability.

The entry "Y" means that the corresponding composition could not be cured by mixing with the specific Paste A; neither a setting time nor a flexural strength could be determined. The entry "Y" accordingly characterizes samples, the constituents of which do not fulfil the requirements of an initiator system.

The test results combined in table 7 and table 8 prove the effects cited below.

The composition B-C1 closely based on the state of the art, which is a comparative composition of particular importance, is polymerized after storing for 6 weeks. This means that the composition from this moment is unusable under the experimental conditions chosen; the storage stability can be evaluated as "mediocre".

Even if (starting from B-C1) according to the invention a small amount of AA is exchanged through NaTS, a pronounced improvement in the storage stability is however shown and even after 12 weeks corresponding compositions according to the invention can still be cured (cf in particular B-I1 to B-I4).

Within this context, the initial curing time is advantageously only insignificantly influenced in comparison with B-C1 through the addition of NaTS, even with large amounts of NaTS (cf, for example, B-I3). This is particularly surprising since NaTS alone (see B-C2) does not fulfil the requirements of a constituent of an initiator system under the chosen experimental conditions and B-C2 cannot be cured by mixing with the assigned Paste A. Only for very high amounts of NaTS (cf B-I4) is the performance impaired in compositions according to the invention after very long storage times of 12 weeks, the consequence of which is that the corresponding resin-modified glass ionomer cement is no longer sufficiently cured.

Particularly favorable flexural strengths and curing times are obtained if the ratio of the total molar amount of AA to the total molar amount of NaTS is greater than 1 (cf table 6, B-I1 and B-I2) or lies in the range from 1 to 10 (cf B-I2).

The results for B-I5 and B-I6 show that the technical effect can be achieved for all of the compounds (A) and (S) to be used according to the invention.

The comparative examples B-C3 and B-C5 show that the technical effect achieved according to the invention cannot be achieved with any mixtures of normal reducing agents. The replacement of AA with NaDS or OA leads, in comparison with B-C1, not to an improved storage stability (cf B-C5) or even to a worsened storage stability (B-C3).

Accordingly, even through the combination of NaTS with OA (cf B-C4) or Fe(II) (cf B-C6 and B-C7), no compositions can be obtained which are sufficiently high-performance to bring about the curing of the resin-modified glass ionomer cement and/or which are stable on storage.

To summarize, it can be established that a composition according to the invention for use as component of a multicomponent resin-modified glass ionomer cement and also the corresponding multicomponent resin-modified glass ionomer cements according to the invention exhibit, in comparison with the systems known from the state of the art, a higher storage stability and also, after storing for several weeks, can be cured with only insignificantly changed setting times to give dental materials which exhibit good mechanical properties, in particular a high flexural strength.

In addition, it is shown that, by the use of compounds (S) selected from the group consisting of sulfinic acids, salts of sulfinic acids and salts of organoboron compounds, the storage stability of compositions comprising one or more compounds (A) selected from the group consisting of the isomers of ascorbic acid, the salts of the isomers of ascorbic acid, the esters of the isomers of ascorbic acid and the ethers of the isomers of ascorbic acid, and also one or more radically polymerizable monomers (M), can be increased.

The invention claimed is:

1. A composition for use in a multicomponent resin-modified glass ionomer cement, the composition comprising
    at least one inhibitor selected from the group consisting of 2,6-di(tert-butyl)hydroxytoluene, hydroquinone monomethyl ether, a 2,2-diphenyl-1-picrylhydrazyl radical, a galvinoxyl radical, a triphenylmethyl radical and a 2,2,6,6-tetramethylpiperidinyl-1-oxyl radical,
    a basic glass composition (G) comprising aluminum fluorosilicate glass,
    one or more radically polymerizable organic monomers (M) comprising monomers with at least two ethylenic groups (M1) and hydroxyl compounds with at least one ethylenic group (M2), and as constituent of a polymerization initiator system
one or more compounds (A) selected from the group consisting of ascorbic acid, salts of ascorbic acid, isomers of ascorbic acid, salts of isomers of ascorbic acid, esters of isomers of ascorbic acid and ethers of isomers of ascorbic acid
and
one or more compounds (S) selected from the group consisting of sulfinic acids, salts of sulfinic acids and salts of organoboron compounds,
wherein, directly after mixing the ingredients, the composition exhibits a viscosity which is smaller at the most by the factor 5, than the viscosity of the composition after being stored at 37° C. for 6 weeks, wherein:
the composition is a liquid or a paste,
ascorbic acid and/or sodium isoascorbate is present in a total amount of 0.1 to 1% by weight,
sodium toluenesulfinate and/or sodium tetraphenylborate is present in a total amount of 0.01 to 1% by weight,
the monomers with at least two ethylenic groups (M1) comprise urethane dimethacrylate and/or triethylene glycol dimethacrylate and/or glycerol 1,3-dimethacrylate in a total amount of 5 to 20% by weight,
the aluminum fluorosilicate glass is present in an amount of 50 to 75% by weight, and
the hydroxyl compounds with at least one ethylenic group (M2) comprise 2-hydroxyethyl methacrylate and/or 2-hydroxypropyl methacrylate in a total amount of 10 to 30% by weight, wherein the percentage values are based on the total weight of the composition.

2. The composition as claimed in claim 1, wherein the basic glass composition (G) is capable of functioning as a crosslinking agent for polymers containing carboxylic acid groups (P) selected from the group consisting of homo- and copolymers of an α,β-unsaturated carboxylic acid (C).

3. The composition as claimed in claim 2,
wherein the aluminum fluorosilicate glass in the basic glass composition is organically modified on its surface and/or the basic glass composition comprises additional one or more other glasses with organically modified surfaces.

4. The composition as claimed in claim 1,
wherein the hydroxyl compounds with at least one ethylenic group (M2) further comprises a compound selected from the group consisting of 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate, and 2,2-bis[4-[3-methacryloyloxy-2-hydroxypropoxy]phenyl]propane.

5. The composition as claimed in claim 1, wherein the ratio of the total molar amount of all of the compounds (A) to the total molar amount of all of the compounds (S)
is greater than 0.2, and/or
is in the range from 0.2 to 50,
and/or
wherein the ratio of the combined total weight of all of the compounds (A) and all of the compounds (S) to the total weight of all of the radically polymerizable organic monomers (M) lies in the range from 0.05 to 10% by weight,
and/or
wherein the total content of radically polymerizable organic monomers (M) lies in the range from 15 to 95% by weight,
and/or
wherein the combined total content of all of the compounds (A) and all of the compounds (S) lies in the range from 0.11 to 7% by weight, based on the total weight of the composition
and/or
wherein the composition
after storing at 37° C. for 6 weeks, has a viscosity which is smaller than 10 000 Pa·s,
and/or
wherein, directly after mixing the ingredients, the composition exhibits a viscosity which is smaller at the most by a factor of 3 than the viscosity of the corresponding composition after storing at 37° C. for 6 weeks.

6. The composition as claimed in claim 1, the composition being anhydrous
and/or
the composition not comprising any polymer containing carboxylic acid groups (P) selected from the group consisting of homo- and copolymers of an α,β-unsaturated carboxylic acid (C)
and/or
the composition not comprising any oxidizing agent (O) selected from the group consisting of persulfates, permanganates, perborates, peroxides and hydroperoxides.

7. A multicomponent resin-modified glass ionomer cement comprising
the composition as claimed in claim 1 as first component and
in one or more additional components, at least
one or more polymers containing carboxylic acid groups (P) selected from the group consisting of homo- and copolymers of an α,β-unsaturated carboxylic acid (C),
water
and
one or more oxidizing agents (O) selected from the group consisting of persulfates, permanganates, perborates, peroxides and hydroperoxides,
wherein the multicomponent resin-modified glass ionomer cement
comprising, in the first and/or additional component, a basic glass composition (G) as crosslinking agent for the polymers (P),
with the proviso that the basic glass composition (G) is not present in a component together with a polymer containing carboxylic acid groups (P) and/or together with water.

8. The multicomponent resin-modified glass ionomer cement as claimed in claim 7, wherein the α,β-unsaturated carboxylic acid (C) is selected from the group consisting of acrylic acid, methacrylic acid, itaconic acid, fumaric acid, maleic acid, chloromethacrylic acid, cyanomethacrylic acid, aconitic acid, mesaconic acid, glutaconic acid and citraconic acid,
and/or
wherein the weight-average molecular weight Mw of the total amount of the polymers containing carboxylic acid groups (P) lies in the range from 1000 to 150 000 g/mol,
and/or
wherein the aluminum fluorosilicate glass in the basic glass composition (G) is organically modified on its surface and/or the basic glass composition comprises one or more other glasses with organically modified surfaces, and/or wherein the one or at least one of the oxidizing agents (O) is selected from the group consisting of peroxides and hydroperoxides.

9. The composition as claimed in claim 1, wherein the composition comprises 0.01 to 1% by weight of 2,6-di(tert-butyl)hydroxytoluene, wherein the percentage values are based on the total weight of the composition.

10. The composition as claimed in claim 1, wherein the ratio of the total molar amount of all of the compounds (A) to the total molar amount of all of the compounds (S) is in the range from 0.3 to 20, and wherein the ratio of the combined total weight of all of the compounds (A) and all of the compounds (S) to the total weight of all of the radically polymerizable organic monomers (M) lies in the range from 0.05 to 10% by weight.

11. The composition as claimed in claim 10, wherein the combined total content of all of the compounds (A) and of all of the compounds (S) lies in the range from 0.11 to 7% by weight, based on the total weight of the composition manufactured.

12. The composition as claimed in claim 1, wherein the combined total content of all of the compounds (A) and of all of the compounds (S) lies in the range from 0.11 to 7% by weight, based on the total weight of the composition manufactured.

13. The composition as claimed in claim 1, wherein:

the one or more compounds (A) are selected from the group consisting of ascorbic acid, sodium ascorbate, isoascorbic acid and sodium isoascorbate, and are present in a total amount of 0.1 to 5% by weight;

the one or more compounds (S) are selected from the group consisting of toluenesulfinic acid, sodium toluenesulfinate, potassium toluenesulfinate, benzenesulfinic acid, sodium benzensulfinate, potassium benzenesulfinate, sodium tetraphenylborate and lithium tetraphenylborate, and are present in a total amount of 0.01 to 5% by weight;

the one or more compounds (M1) are selected from the group consisting of ethylene glycol dimethacrylate, 1,6-hexanediol dimethacrylate, triethylene glycol dimethacrylate, 1,12-dodecanediol dimethacrylate, ethoxylated bisphenol A dimethacrylate, polyethylene glycol dimethacrylate, 7,7,9-trimethyl-4,13-dioxo-3,14-dioxa-5,12-diazahexadecane-1,16-diol dimethacrylate, butanediol dimethacrylate, trimethylolpropane trimethacrylate, urethane dimethacrylate, glycerol 1,3-dimethacrylate, tetraethylene glycol dimethacrylate, neopentyl glycol dimethacrylate, 2,2-bis[4-[3-methacryloyloxy-2-hydroxypropoxy]phenyl]propane and di(meth)acrylates of dihydroxymethyltricyclo[$5.2.1.0^{2,6}$]decane, and are present in a total amount of 5 to 40% by weight;

the one or more compounds (M2) are selected from the group consisting of 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl 1,3-dimethacrylate, 3-hydroxypropyl 1,2-dimethacrylate, pentaerythritol dimethacrylate, glycerol dimethacrylate, and 2,2-bis[4-[3-methacryloyloxy-2-hydroxypropoxy]phenyl]propane, and are present in a total amount of 10 to 60% by weight, wherein the percentage values are based on the total weight of the composition.

* * * * *